(12) United States Patent
Swager et al.

(10) Patent No.: US 8,999,722 B2
(45) Date of Patent: Apr. 7, 2015

(54) DETECTION OF ANALYTES INCLUDING NITRO-CONTAINING ANALYTES

(75) Inventors: Timothy M. Swager, Newton, MA (US); Trisha L. Andrew, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 241 days.

(21) Appl. No.: 13/574,207

(22) PCT Filed: Mar. 30, 2012

(86) PCT No.: PCT/US2012/031491
§ 371 (c)(1),
(2), (4) Date: Jul. 19, 2012

(87) PCT Pub. No.: WO2013/022494
PCT Pub. Date: Feb. 14, 2013

(65) Prior Publication Data
US 2013/0065318 A1    Mar. 14, 2013

Related U.S. Application Data

(60) Provisional application No. 61/469,538, filed on Mar. 30, 2011.

(51) Int. Cl.
*G01N 21/64* (2006.01)
*G01N 21/00* (2006.01)

(52) U.S. Cl.
CPC .......... *G01N 21/643* (2013.01); *G01N 21/6408* (2013.01); *G01N 2021/6439* (2013.01); *G01N 2021/6441* (2013.01)

(58) Field of Classification Search
CPC ..... G01N 21/643; G01N 21/64; G01N 21/63; G01N 21/62; G01N 2120/6408; G01N 21/6408
USPC ............... 436/116, 112, 111, 106; 422/82.05, 422/68.1, 50
See application file for complete search history.

(56) References Cited

U.S. PATENT DOCUMENTS

| 7,666,684 B2 | 2/2010 | Swager et al. | |
| 2010/0022011 A1* | 1/2010 | Swager et al. | ................. 436/81 |
| 2010/0303672 A1 | 12/2010 | Swager et al. | |

OTHER PUBLICATIONS

International Search Report for PCT/US2012/031491 obtained on Jun. 3, 2012, p. 1-8.*
International Search Report and Written Opinion for PCT/US2012/31491 mailed Jan. 24, 2013.
Andrew et al., Detection of explosives via photolytic cleavage of nitroesters and nitramines. J Org Chem. May 6, 2011;76(9):2976-93. Epub Mar. 31, 2011.

(Continued)

*Primary Examiner* — Christine T Mui
(74) *Attorney, Agent, or Firm* — Wolf, Greenfield & Sacks, P.C.

(57) ABSTRACT

Sensors and methods for determination of analytes are provided. Analytes including explosives (e.g., RDX or PETN) may be determined by monitoring, for example, a change in an optical signal of a material upon exposure to the analyte. In some embodiments, the analyte and the material may interact via a chemical reaction to form a new emissive species. Embodiments described herein may provide inexpensive sensors with high selectivity and sensitivity.

81 Claims, 19 Drawing Sheets

(56) References Cited

OTHER PUBLICATIONS

Andrew et al., A fluorescence turn-on mechanism to detect high explosives RDX and PETN. J Am Chem Soc. Jun. 13, 2007;129(23):7254-5.

Andrew, Design and synthesis of organic chromophores for imaging, lithography and organic electronics. Ph.D. Thesis, The Massachusetts Institute of Technology. Feb. 2011. 238 pages.

Craig et al., The Nitro and Amino Derivatives of t-Butylbenzene. J Am Chem Soc. 1935;57:195-8.

Crosby et al., The measurement of photoluminescence quantum yields. J Phys Chem. 1971;75:991-1024.

Hatchard et al., A New Sensitive Chemical Actinometer. II. Potassium Ferrioxalate as a Standard Chemical Actinometer. Proc R Soc London A. 1956;235:518-36.

Hill et al., A mechanistic study of the photochemically initiated oxidative addition of isopropyl iodide to dimethyl(1,10-phenanthroline)platinum(II). J Am Chem Soc. 1985;107:1218-25.

Sheldrick, Phase annealing in SHELX-90: direct methods for larger structures. Acta Cryst. 1990;A46:467-73.

International Preliminary Report on Patentability mailed Mar. 27, 2014 for International Application No. PCT/US2012/031491.

\* cited by examiner

Photoreduction of RDX/PETN by Hydride Donors:

Nitration of Aromatic Amines by the Photodegradation Products of RDX/PETN:

DHA1 R = H, R' = Me
DHA5 R = Me, R' = Me
DHA4 R = H, R' = Ph
DHA8 R = Me, R' = Ph
DHA18 R = 2-mesityl, R' = Me 26 R = H, R' = Me
27 R = Me, R' = Me
28 R = H, R' = Ph
29 R = Me, R' = Ph
30 R = 2-mesityl, R' = Me DHA2 R = H
DHA6 R = Me 31 R = H
32 R = Me 33 R = H
34 R = Me

DETECTION OF ANALYTES INCLUDING NITRO-CONTAINING ANALYTES

STATEMENT REGARDING FEDERALLY SPONSORED RESEARCH OR DEVELOPMENT

This invention was made with government support under Grant No. ECCS-0731100, awarded by the National Science Foundation, and under Grant No. W911NF-07-1-0654, awarded by the Army Research Office. The government has certain rights in this invention.

RELATED APPLICATIONS

This application is a national stage filing under 35 U.S.C. §371 of International PCT Application No. PCT/US2012/031491, filed Mar. 30, 2012, entitled "Detection of Analytes Including Nitro-Containing Analytes," by Swager et al., which claims the benefit under 35 U.S.C. §119(e) of U.S. Provisional Patent Application Ser. No. 61/469,538, filed Mar. 30, 2011, entitled "Detection of Analytes Including Nitro-Containing Analytes," by Swager, et al., the contents of each which are incorporated herein by reference.

FIELD OF THE INVENTION

Devices and methods for the determination of analytes, including 1,3,5-trinitrotriazinane (RDX), and pentaerythritol tetranitrate (PETN), are provided.

BACKGROUND OF THE INVENTION

Detecting hidden explosive devices in war zones and transportation hubs is an important pursuit. Commonly-used, highly energetic compounds found in explosive formulations include 2,4,6-trinitrotoluene (TNT), 1,3,5-trinitrotriazinane (RDX), and pentaerythritol tetranitrate (PETN). Existing technologies for detecting the energetic chemical components of explosive devices, including analytical spot tests, fluorescent sensors using either small-molecule fluorophores or fluorescent conjugated polymers, chemiresistive sensors, portable mass spectrometers, and X-ray systems, often have limitations. For instance, while X-ray systems are capable of detecting bulk hidden explosive devices and portable mass spectrometers are capable of identifying the exact chemical structures of suspect chemicals, the practical deployment and/or longevity of these hardware-intensive technologies in complex environments is non-trivial.

Fluorescent sensors are comparatively technology-unintensive, have desirably low detection limits and the ability to identify (e.g., respond to) entire classes of molecules (such as nitroaromatics) or particular functional groups (vide infra). Chemical spot tests can be specific but are not as sensitive as fluorescent sensors and generally do not have the analytical advantages of an emissive signal, such as remote line-of-sight (e.g., stand-off) detection or prospects for complex signal processing (i.e., fluorescence lifetimes, depolarization).

Nitroesters and nitramines have been known to degrade under highly acidic or basic conditions, and methods for detect these chemical degradation products have been studied. The base-promoted digestion of nitroglycerin (NG) has also been studied and is thought to evolve a mixture of nitrate and nitrite anions, among other degradation products. (FIG. 1A) Similarly, RDX is also known to decompose in basic media and produce nitrite ions. The commercially-available Greiss test for nitrite ions has been employed to detect the evolution of nitrite upon base-promoted degradation of RDX and PETN. (FIG. 1B) FIG. 1C shows the components of the Greiss test, including sulfanilamide 4 and arylamine 5. The Greiss test involves the reaction of sulfanilamide 4 with nitrite to form diazonium salt 6, which then reacts with an arylamine 5 to form a brightly-colored azo dye (7). Similar tests conducted in the absence of a base have indicated that nitrite ions may be generated upon the photolysis of RDX and PETN.

Unfortunately, the Greiss test or variations thereof have certain disadvantages in the detection of explosives such as RDX and PETN. For example, simple standoff detection (i.e., detection at a distance) with colorimetric spot tests is limited by the difficulty in getting a clear optical signal returned from a purely absorptive process. Moreover, even with optimized reagent systems, the detection limit of the Greiss test is in the microgram regime, which is generally not competitive with existing methods to detect RDX and PETN.

SUMMARY OF THE INVENTION

Devices and methods relating to the determination of analyte are provided. In some embodiments, sensors are provided. In some embodiments, the sensor comprises a material comprising a compound capable of accepting a nitro equivalent upon exposure to a nitro-containing analyte; a source of energy applicable to the material to cause an emission of radiation; and an emission detector positioned to detect the emission.

In some embodiments, the sensor comprises a compound comprising the structure,

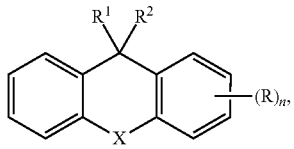

wherein X is a heteroatom optionally substituted with hydrogen, alkyl, heteroalkyl, alkenyl, heteroalkenyl, alkynyl, heteroalkynyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, or heteroaryl, any of which is optionally substituted; and n is 0-8; a source of energy applicable to the compound to cause an emission of radiation; and an emission detector positioned to detect the emission.

In some embodiments, methods for determining an analyte are provided. In some embodiments, the method may comprise exposing a material to a sample suspected of containing an analyte, wherein the analyte, if present, interacts with the material via a nitration reaction to produce a nitro-containing compound having a luminescence emission; and determining the luminescence emission of the compound, thereby determining the analyte.

In some embodiments, the method may comprise exposing a material to a sample suspected of containing an analyte, wherein the analyte, if present, interacts with the material to produce a change in a determinable signal of the material, wherein the material comprises a compound having the structure,

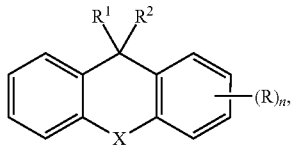

wherein X is a heteroatom optionally substituted with alkyl, heteroalkyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, or heteroaryl, any of which is optionally substituted; and n is 0-8; and determining the change in the determinable signal of the material, thereby determining the analyte.

Figure 1A:
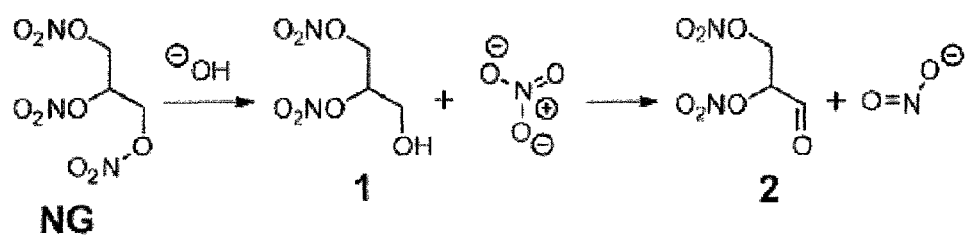
FIG. 1 shows (a) the proposed mechanism for the base-promoted degradation of nitroglycerin; (b) the proposed mechanism for the base-promoted degradation of RDX; (c) the active components of the Greiss test; and (d) the detection mechanism of the Zeller-Greiss test for nitrite ions.
Figure 1B:
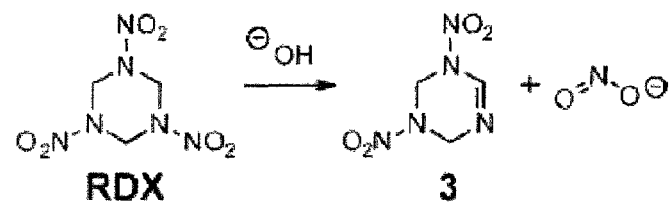
Figure 1C:
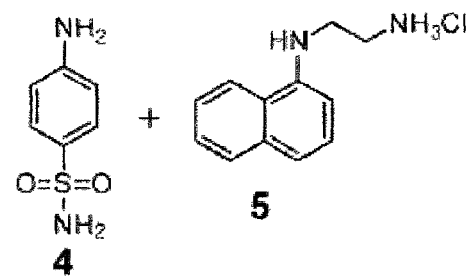
Figure 1D:
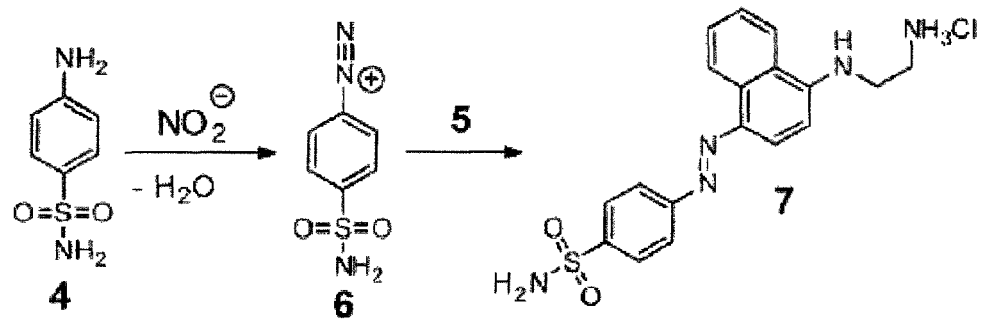

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to sensors and methods involving determination of an analyte.

Analytes may be determined by monitoring, for example, a change in an optical signal of a material upon exposure to an analyte. In some embodiments, the analyte and the material may interact via a chemical reaction, or other chemical, biochemical or biological interaction (e.g., recognition), to form a new emissive species. In some cases, embodiments described herein may be useful in the detection of analytes such as explosives (e.g., RDX or PETN). Methods described herein may be advantageous in that the high sensitivity of luminescence (e.g., fluorescence) spectroscopy can allow for the reliable detection of small changes in luminescence intensity. Some embodiments provide inexpensive indicators for the selective, standoff identification of analytes, such as nitroester and nitramine explosives.

Embodiments described herein may be particularly advantageous in that analytes which do not readily interact with luminescent materials via, for example, pi-stacking interactions, may be determined. As used herein, "pi-stacking interactions" refer to cofacial interactions between pi-orbitals of conjugated species. Examples of such analytes include those which are, for example, non-planar, non-aromatic, and/or have relatively high reduction potentials (i.e., weak electron affinity). In some cases, the analyte may be an explosive. For example, 2,4,6-hexahydro-1,3,5-triazinane (RDX) may be characterized by a non-planar, three-dimensional structure, making it difficult for RDX to engage in pi-stacking interactions with luminescent materials having pi-conjugated moieties. Other non-planar, non-aromatic analytes may include 2,3-dimethyl-2,3-dinitrobutane (DMNB), 2,2-bis[(nitrooxy)-methyl]-1,3-propanediol dinitrate ester (pentaerythritol tetranitrate or PETN), 1,3,5,7-tetranitroperhydro-1,3,5,7-tetrazocine (HMX), nitroamines, nitroamides, nitroesters, other nitro- or nitrate-containing species, and the like. Embodiments described herein may also be advantageous since, in some cases, a new and/or enhanced signal may be generated in the presence of analyte (e.g., a "turn-on" detection mechanism), allowing for higher sensitivity in the determination of analytes.

In some embodiments, methods for determining analytes are provided. The method may involve exposure of a material to a sample suspected of containing an analyte (e.g., a nitro-containing analyte), and, if present, the analyte, or a species generated by the analyte, interacts with at least a portion of the material to cause a change in a determinable signal of the material. Determination of the change in signal may then determine the analyte. The determinable signal may be a chemical, optical, electrochemical, or other physical characteristic associated with the material. In some cases, the determinable signal may be a luminescence emission, such as fluorescence. For example, the change may comprise a decrease in the luminescence intensity of the material. In some embodiments, the change comprises an increase in luminescence intensity of the material. In some embodiments, the change comprises a shift in the wavelength of the luminescence emission. As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction.

The analyte or species generated by the analyte may interact with the material in various ways, including binding interactions, electrostatic interactions, chemical reactions, energy transfer, or the like. In some embodiments, the interaction between the material and the analyte or species generated by the analyte may comprise a binding interaction (e.g., dative binding, biological binding). In some embodiments, the interaction between the material and the analyte or species generated by the analyte may comprise one or more chemical reactions. For example, a chemical reaction may occur between the compound and the analyte, or species generated by the analyte, to produce a product having a determinable signal that is different than that of the compound in the absence of analyte. For example, the compound may have little or substantially no luminescence emission in the absence of analyte, and, in the presence of analyte, a chemical reaction may occur between the compound and the analyte, or species generated by the analyte, to produce a product having an enhanced luminescence emission. In some embodiments, a chemical reaction may occur upon exposure of the compound and analyte to electromagnetic radiation (e.g., a photochemical reaction).

In some embodiments, the interaction between the compound and the analyte may comprise a nitration reaction, i.e., a reaction in which a nitro equivalent is transferred from one species to another, producing a nitro-containing compound. As used herein, a "nitro equivalent" refers to one or more species which form the net equivalent of a nitro group (e.g., "—$NO_2$"). The nitro equivalent may include a nitrate ion, a nitrite ion, a nitronium ion, or any other combination of species which may react with the compound to produce a nitro-containing compound. The term "nitro-containing compound" refers to a species comprising —$NO_2$ group. In some embodiments, the compound accepts a nitro equivalent from the analyte or species generated by the analyte. Some embodiments involve the transfer of at least one nitro equivalent to the compound. In some cases, the compound may accept one nitro equivalent. For example, the compound may be an aromatic compound, which may be nitrated in the presence of analyte to produce a nitroaromatic compound. In an illustrative embodiment, both N,N-dimethylaniline and 9,9-disubstituted 9,10-dihydroacridines (DHAs) are capable of being nitrated by reactive, electrophilic $NO_x$ photofragmentation products of RDX and PETN to yield a singly-nitrated product. In some cases, the compound may accept more than one nitro equivalent.

Figure 2:
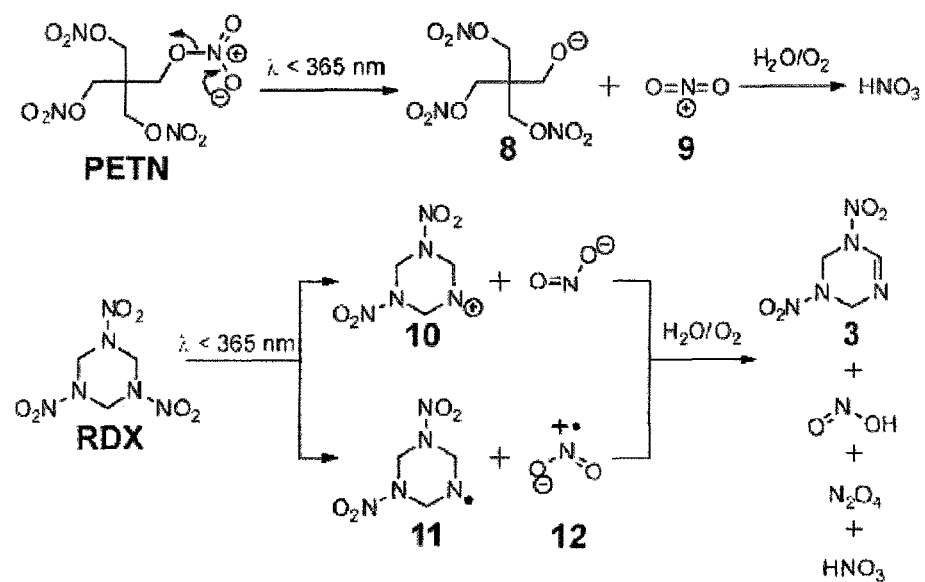
FIG. 2 shows the proposed photolytic degradation mechanisms for PETN and RDX.
Figure 3A:
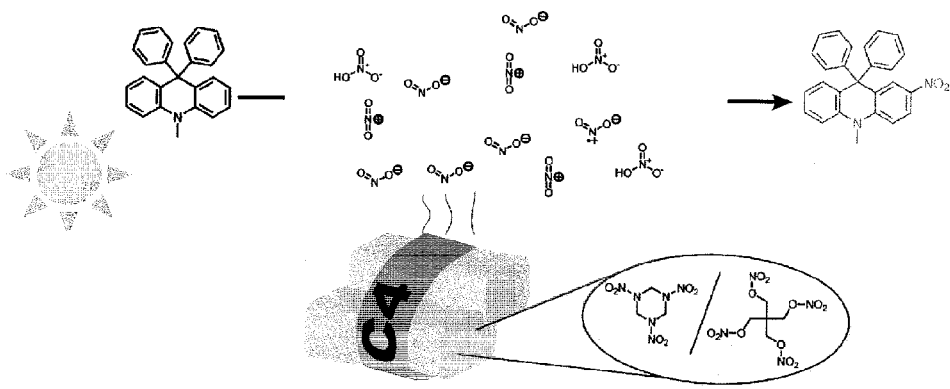
FIG. 3 illustrates (a) a detection scheme involving transfer of a nitro equivalent from an analyte to a compound and (b) examples of compounds useful in the detection of analytes.
Figure 3B:
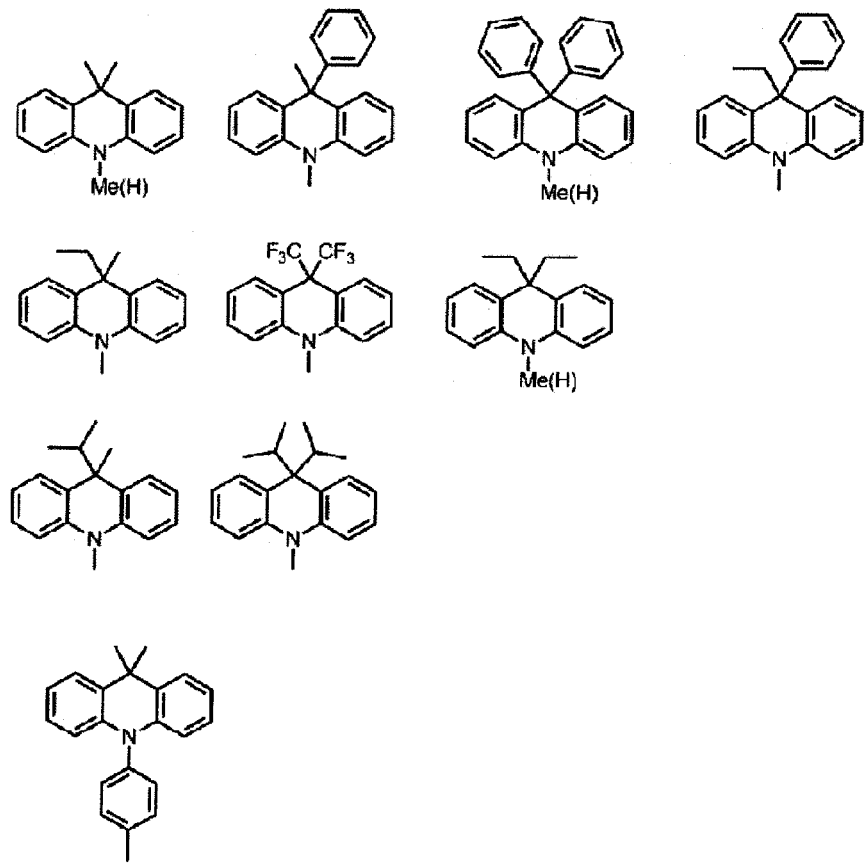

In some cases, the analyte may produce a species capable of transferring a nitro equivalent to, i.e., nitrating, the compound. For example, upon exposure to a source of energy, the analyte may donate or release a nitro equivalent, which may then interact with the compound to produce a nitro-containing compound. In one set of embodiments, the analyte may undergo a photochemical reaction upon exposure to electromagnetic radiation causing the analyte to produce reactive, electrophilic species which may then react with the compound via a nitration reaction. The species may be, for example, a $NO_x$ species where x is at least 1. In some embodiments, the species is a nitrate ion. In some embodiments, the species is a nitrite ion. In some embodiments, the species is a nitronium ion. For example, the photolysis of nitroester and nitramine-based compounds under various conditions has been found to produce a number of small-molecule degradation products, including nitrous and nitric acid, nitric oxide, nitrogen dioxide, formaldehyde and ammonia. In an illustrative embodiment, the nitramine-containing explosive RDX and the nitroester-containing explosive PETN photofragment upon exposure to electromagnetic radiation to produce reactive $NO_x$ species, such as nitrogen dioxide and nitric acid. (FIG. 2) Without wishing to be bound by theory, FIG. 2 illustrates how, in the case of PETN, heterolytic cleavage of the O—$NO_2$ bond may produce alkoxide 8 and highly reactive nitronium ion 9 that rapidly forms nitric acid under ambient conditions. For RDX, both the homolytic and heterolytic scission of the N—$NO_2$ bond of RDX may produce nitrogen dioxide 12 or nitrite, respectively.

In some cases, the analyte may produce the species (e.g., nitro equivalent) upon exposure to a source of energy. The source of energy may be an electric, magnetic, optical, acoustic, electromagnetic, or mechanical field. In some embodiments, the source of energy is electromagnetic radiation. Application of the source of energy to the compound and analyte may cause the analyte to produce the reactive species and may also produce an emission of radiation from the resulting nitro-containing compound. In other embodiments, more than one source of energy may be utilized. For example, a first source of energy may be applied to the analyte to produce the reactive species and a second, different source of energy may be applied to the resulting nitro-containing compound to produce an emission of radiation. The first and second sources of energy may be different forms of energy or may be similar sources of energy having different characteristics. For example, the first and second sources of energy may be electromagnetic radiation of different wavelengths. It should be understood that the use of electromagnetic radiation is described by way of example only, and those of ordinary skill in the art would be capable of selecting other sources of energy to effect other types of chemical reactions or to generate other types of determinable signals. As an example, the source of energy may be an electric field which may produce a signal based on conductivity, resistivity, or the like.

Upon reaction with the analyte or species produced by the analyte, a species having a determinable signal may be produced. In some embodiments, the signal may be a luminescence emission. For example, the compound may react with the analyte, or species produced by the analyte, to produce a nitro-containing compound having a luminescence emission. In some embodiments, the compound may have a relatively low or substantially no luminescence emission, and, upon exposure to the analyte, the resulting nitro-containing compound may have a new luminescence emission.

In some embodiments, the luminescence of the material may be increased upon exposure to the analyte and a source of energy, relative to the luminescence of the material prior to exposure to the analyte (e.g., a "turn-on" emission signal). For example, the nitro-containing compound may have a luminescence emission signal that is increased relative to that of the essentially identical compound lacking the nitro group prior to exposure to the analyte. In some cases, the luminescence of the material may be decreased upon exposure to the analyte and a source of energy, relative to the luminescence of the material prior to exposure to the analyte (e.g., a "turn-off" emission signal). In some embodiments, the material comprising the nitro-containing compound (e.g., after exposure to the analyte) has a luminescence intensity at 550 nm that is about 5-fold, 10-fold, 15-fold, 20-fold, 25-fold, or 50-fold greater than that of material prior to exposure to the analyte. In some embodiments, the material comprising the nitro-containing compound (e.g., after exposure to the analyte) has a luminescence intensity at about 300 nm, about 310 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, or about 650 nm, that is about 5-fold, 10-fold, 15-fold, 20-fold, 25-fold, or 50-fold greater than that of material prior to exposure to the analyte.

Methods described herein are capable of rapidly generating a determinable signal in response to an analyte. In some embodiments, the method may involve exposing both a compound as described herein and a sample suspected of containing an analyte to electromagnetic radiation for a period of an hour or less, 45 minutes or less, 30 minutes or less, 15 minutes or less, 10 minutes or less, 5 minutes or less, 3 minutes or less, 1 minute or less, or, in some cases, 30 seconds or less, 15 seconds or less, or 5 seconds or less. In some embodiments, the compound and the sample suspected of containing the analyte may be exposed to electromagnetic radiation for a period of about 30 seconds to about 5 minutes.

Compounds suitable for use in sensors and methods as described herein include compounds which are capable of accepting a nitro equivalent upon exposure to an analyte and a source of energy, such as electromagnetic radiation. For example, the compound may have sufficient nucleophilicity and/or electron density to accept or form a bond with an electrophilic nitro equivalent. In some cases, the compound may comprise an aromatic group (e.g., a phenyl group) capable of accepting a nitro equivalent. In some cases, the compound may be a luminescent compound prior to exposure to an analyte. In some cases, the compound may be substantially non-emissive prior to exposure to an analyte. For example, the compound may form an emissive, nitro-containing moiety upon acceptance of a nitro equivalent from the analyte. In some cases, the compound may be selected to have sufficient electron density such that, upon nitration, donor-acceptor chromophores possessing high fluorescence quantum yields may be formed. In some cases, the compound may be selected to have sufficient structural rigidity to accommodate a donor-acceptor pair. In some embodiments, at least a portion of the compound may comprise a monocyclic or polycyclic aromatic group, including aryl and heteroaryl groups. In some embodiments, the compound may comprise a heterocycle. Examples of compounds suitable for use in the invention include, but are not limited to, 1,4-dihydroquinolines, 9,10-dihydroacridines, and the like.

In some embodiments, the compound is a 9,10-dihydroacridine. For example, the compound may comprise the structure,

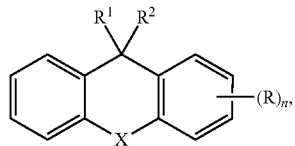

wherein X is a heteroatom optionally substituted with hydrogen, alkyl, heteroalkyl, alkenyl, heteroalkenyl, alkynyl, heteroalkynyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, or heteroaryl, any of which is optionally substituted; and n is 0-8. In some embodiments $R^1$ and $R^2$ are can be the same or different and are alkyl or aryl, any of which is optionally substituted. In some embodiments, both $R^1$ and $R^2$ are the same. In some cases, both $R^1$ and $R^2$ are not hydrogen.

In some cases, wherein X is a heteroatom optionally substituted with hydrogen, alkyl, heteroalkyl, alkenyl, heteroalkenyl, alkynyl, heteroalkynyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, alkenyl, or heteroaryl, any of which is optionally substituted; and n is 0-8.

In some embodiments, $R^1$ and/or $R^2$ are optionally substituted alkyl. For example, the alkyl group may be methyl, ethyl, propyl, isopropyl, or the like. In some embodiments, $R^1$ and/or $R^2$ are optionally substituted alkenyl (e.g., vinyl). In some embodiments, $R^1$ or $R^2$ are optionally substituted aryl. For example, the aryl group may be phenyl, naphthyl, or the like. In one set of embodiments, $R^1$ and $R^2$ are phenyl. Such groups may optionally substituted, for example, with alkyl groups, halogenated alkyl groups (e.g., —$CF_3$), aryl groups, halogenated aryl groups, alkyl-substituted aryl groups (e.g., mesityl), and the like.

In some embodiments, at least two R groups are joined together to form a cycloalkyl, heterocycloalkyl, aryl, or heteroaryl ring, any of which is optionally substituted.

In some embodiments, X is nitrogen, oxygen, sulfur, or phosphorus, any of which is optionally substituted. In some embodiments, X is an optionally substituted nitrogen. In some embodiments, X is nitrogen optionally substituted with hydrogen, alkyl, heteroalkyl, alkenyl, heteroalkenyl, alkynyl, heteroalkynyl, aryl, or heteroaryl, each optionally substituted. For example, X may be NH, N-methyl, N-phenyl, or the like. In some embodiments, X is oxygen. In some embodiments, X is sulfur. In some embodiments, X is phosphorus, optionally substituted.

In some embodiments, n is 0, 1, 2, 3, 4, 5, 6, 7, and/or 8. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8.

In one set of embodiments, the compound has the structure,

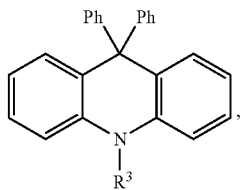

wherein $R^3$ is hydrogen or alkyl.

In one embodiment, the compound has the structure,

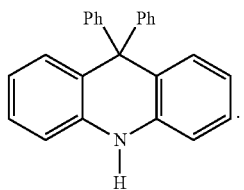

In one embodiment; the compound has the structure,

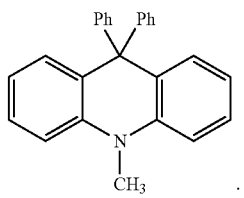 [SMILES: CN1c2ccccc2C(c2ccccc2)(c2ccccc2)c2ccccc21]

In some cases, the method may comprise determining a change in the wavelength of an emission signal. For example, the interaction between the analyte and the compound may cause a shift in the wavelength of the luminescence intensity of the compound. That is, in the absence of analyte, the compound may have a first emission upon exposure to electromagnetic radiation, and, upon exposure to an analyte, the analyte may interact with at least a portion of the compound such that a second emission signal is generated at a different wavelength. The difference in the wavelengths of the first emission and the second emission may be at least 30 nm, or, in some embodiments, at least 50 nm, at least 75 nm, at least 100 nm, or at least 150 nm. The wavelength of an emission signal refers to the wavelength at which the peak maximum of the emission signal occurs in an emission spectrum. The emission signal may be a particular peak having the largest intensity in an emission spectrum (e.g. a fluorescence spectrum), or, alternatively, the emission signal may be a peak in an emission spectrum that has at least a defined maximum, but has a smaller intensity relative to other peaks in the emission spectrum. In some cases, upon exposure to the analyte, the second emission signal may be generated at a wavelength having substantially no emission signal in the absence of analyte.

In some embodiments, methods of the invention comprise determining a change in the luminescence intensity of an emission signal. In some embodiments, the change may be a decrease in luminescence intensity. In some embodiments, the change may be an increase in luminescence intensity. For example, the compound may have a low or substantially no emission in the absence of analyte, and, upon exposure to the analyte, the emission signal may increase or a new emission signal may be generated (e.g., a "turn-on" detection mechanism). The change in luminescence intensity may occur for an emission signal with substantially no shift in the wavelength of the luminescence (e.g., emission), wherein the intensity of the emission signal changes but the wavelength remains essentially unchanged. In other embodiments, the change in luminescence intensity may occur for an emission signal in combination with a shift in the wavelength of the luminescence (e.g., emission). For example, an emission signal may simultaneously undergo a shift in wavelength in addition to an increase or decrease in luminescence intensity. In another embodiment, the change may comprise two emission signals occurring at two different wavelengths, wherein each of the two emission signals undergoes a change in luminescence intensity. In some cases, the two emission signals may undergo changes in luminescence intensity independent of one another. In some cases, the two emission signals may undergo changes in luminescence intensity, wherein the two emission signals are associated with one another, for example, via an energy transfer mechanism, as described more fully below.

Methods of the present invention may comprise determining a change in luminescence intensity in combination with a change in the luminescence wavelength, upon exposure of the compound to an analyte. For example, the relative luminescence intensities of a first emission signal and a second emission signal associated with the first emission signal may be modulated using the methods described herein. In some cases, the first emission signal and the second emission signal may be associated with (e.g., interact with) one another via an energy transfer mechanism, such as fluorescence resonance energy transfer, for example. The term "fluorescence resonance energy transfer" or "FRET" is known in the art and refers to the transfer of excitation energy from an excited state species (i.e., FRET donor) to an acceptor species (i.e., FRET acceptor), wherein an emission is observed from the acceptor species.

In one embodiment, a first luminescent species may act as FRET donor and a second luminescent species may act as a FRET acceptor, wherein the first portion and the second portion each have different emission wavelengths. The first luminescent species may be associated with a quenching molecule and exist in a "quenched" state, wherein, upon exposure of the first portion to electromagnetic radiation, the quenching molecule absorbs the excitation energy and substantially no emission is observed. Upon exposure to an analyte, the analyte may interact with the first luminescent species and/or quenching molecule to "un-quench" the first luminescent species. As a result, exposure of the first luminescent species to electromagnetic radiation produces an excited-state, wherein the first luminescent species may transfer excitation energy to the second luminescent species, and emission signal from the second luminescent species is observed.

In some cases, the emission may also be visible by sight, e.g., the compound may emit visible light. This may allow for the determination of analytes via a colorimetric change. For example, the compound, in the absence of analyte, may have a first color, and, upon exposure to an analyte and irradiation by a source of energy, the compound may have a second color, wherein the change in color may determine the analyte.

In an illustrative embodiment, the compound is N,N-dimethylaniline, which may be nitrated upon exposure to analytes such as RDX and PETN. Photolysis of a mixture of N,N-dimethylaniline and either RDX or PETN in acetonitrile under anaerobic conditions produced the emissive N,N-dimethyl-4-nitroaniline. In another set of embodiments, the compound is a 9,9-disubstituted 9,10-dihydroacridine (DHA) that is rapidly nitrated by the photofragmentation products of RDX and PETN.

Sensors for the determination of analytes are also provided. In some embodiments, the sensor comprise compounds capable of accepting a nitro equivalent upon exposure to an analyte, as described herein. In some cases, the compound is in solution. In some cases, the compound is in solid form. For example, the sensor may further comprise a solid support material, wherein the compound is dispersed within the support material. In some cases, the support material may be a polymer, such as poly(methyl methacrylate). The compound may be attached to the support material via covalent bonds or non-covalent bonds. In some embodiments, the compound may be non-covalently dispersed within the support material. In some cases, the solution or support material may comprise at least 1 wt % of compound, or, in some embodiments, at least 5 wt % of compound, at least 10 wt % of compound, at least 25 wt % of compound. In some embodiments, the solution or support material comprises 10 wt % of compound. In some embodiments, the compound and optionally other components may be formed as a thin film.

The sensor may further comprise at least one source of energy applicable to the compound. In some cases, a first source of energy may cause the analyte to produce one or more reactive species and a second source of energy may cause the compound and/or the nitro-containing compound that is generated upon exposure to the analyte to produce an emission of radiation, wherein the first source of energy and the second source of energy are different. In some cases, a single source of energy may cause the analyte to produce one or more reactive species and may produce an emission of radiation from the compound and/or nitro-containing compound. The source of energy may be an electric, magnetic, optical, acoustic, electromagnetic, or mechanical field. In some embodiments, the source of energy is electromagnetic radiation. The sensor may further comprise an emission detector positioned to detect the emission.

The source of energy can be provided in combination with the compound and/or sensor in a variety of ways, such as being integrally and/or functionally connected to the compound/sensor (for example, by providing a compartment or other assembly supporting both the compound/sensor and the energy source), or in combination such that the compound/sensor and energy source can be used together (e.g., packaged together, or otherwise provided together and with the ability to arrange each, with respect to the other, for use as described herein). The emission detector can be provided in combination with the compound and/or sensor, in a manner as described above with respect to the energy source. Where the energy source and emission detector are both provided in combination with the compound/sensor, they can be provided in essentially identical or similar structural relation to the compound/sensor (e.g., both attached to a common housing or framework, to which the compound/sensor is also attached), or their relationship to the compound/sensor can differ.

In some embodiments, sensors of the invention may comprise an inlet for intake of a sample (e.g., vapor sample, solution sample), a sample cell comprising the compound and constructed and arranged to receive the sample, and a detection mechanism in optical communication with the sample cell. Systems such as this may be useful in the determination of, for example, explosives such as RDX. As used herein, a sample cell "constructed and arranged" refers to a sample cell provided in a manner to direct the passage of a sample, such as a sample comprising RDX, from the inlet into the sample cell, such that the vapor sample contacts the compound. "Optical communication" may refer to the ability of the detection mechanism to receive and detect an optical signal (e.g., light emission) from the sample cell.

As described herein, the compound may be contained in solution or dispersed within a support material. The compound may be dissolved or suspended in any fluid which does not react with the analyte, compound, or intermediates or products thereof, or does not otherwise interfere with the determination of the analyte. The fluid may be aqueous, organic, or combinations thereof. In some embodiments, the fluid is an organic solvent, including polar and non-polar solvents. In one set of embodiments, the fluid is a polar solvent. Examples of fluids suitable for use in this invention include, but are not limited to, alcohols such as methanol, ethanol, and isopropanol, DMSO, DMF, acetonitrile, chloroform, dichloromethane, carbon tetrachloride, benzene, and the like. In one embodiment, the compound may be contained in acetonitrile.

The support material may be any material capable of supporting (e.g., containing) the compounds as described herein. For example, the support material may be selected to have a particular surface area wherein the support material may absorb or otherwise contact a sufficient amount of analyte (e.g., PETN, RDX) to allow interaction between the analyte and, for example, the compound. In some embodiments, the support material has a high surface area. In some cases, the support material has a surface area of at least 50 mm$^2$, at least 100 mm$^2$, at least 200 mm$^2$, at least 300 mm$^2$, at least 400 mm$^2$, or, more preferably, at least 500 mm$^2$.

In some embodiments, the support material may have a low background signal, substantially no background signal, or a background signal which does not substantially interfere with the signal generated by the compound, either in the presence or in the absence of analyte. That is, the support material may be sufficiently optically transparent relative to the emissive compound and/or photochemical products thereof. The support material may be soluble, swellable, or otherwise have sufficient permeability in systems of the invention to permit, for example, intercalation of compounds as described herein, and other components within the support material. In one embodiment, the support material may be hydrophobic, such that a hydrophobic solution containing the compound may diffuse or permeate the support material. In another embodiment, the support material may form a homogeneous solution with the compound. Additionally, the support material may preferably permit efficient contact between the sample (e.g., analyte) to be determined and the compound. For example, in one embodiment, a vapor or solution comprising an analyte may permeate the support material to interact with the compound via a photochemical reaction. The permeability of certain support materials described herein are known in the art, allowing for the selection of a particular support material having a desired diffusion. The choice of support material may also affect the intensity and duration of light emission from the system.

Examples of support materials include polymers, copolymers, gels, and other solid adsorbent materials. In some embodiments, the support material may have a shape or be formed into a shape (for example, by casting, molding, extruding, and the like). In some cases, the support material may be a film. In some embodiments, the support material may be a polymer. Examples include poly(methyl methacrylate), polyethylene, polypropylene, poly(vinyl chloride), poly (vinyl benzoate), poly(vinyl acetate), cellulose, corn starch, poly(vinyl pyrrolidinone)s, polyacrylamides, epoxys, silicones, poly(vinyl butyral)s, polyurethanes, nylons, polacetals or polyacetals, polycarbonates, polyesters and polyethers, polybutadiene copolymers, crosslinked polymers, combinations thereof, and the like. In some cases, the polymer may be a conjugated polymer, such as polyarylenes, polyarylene vinylenes, polyarylene ethynylenes and ladder polymers, i.e. polymers having a backbone that can only be severed by breaking two bonds. In one embodiment, the polymer is poly (methylmethacrylate), poly(vinylpyrrolidinone), or poly(4-vinylpyridine). In one embodiment, the polymer is poly(m-ethylmethacrylate). In one embodiment, the polymer is poly (vinylpyrrolidinone).

The combination of support material and solvent may have a desired diffusion rate, controlling the intensity and duration of light emission. The permeability of a particular polymer is known in the art.

Sensors comprising compounds dispersed (e.g., non-covalently dispersed) within a support material are described herein by way of example only, and it should be understood that, in some cases, other configurations of compounds and support materials may be encompassed within the scope of the invention. For example, the compound may be covalently bonded to the support material, such as a polymer. In some cases, the compound may be covalently bonded to a polymer backbone via a pendant side group. In some cases, the compound may be positioned within a polymer backbone.

The analyte may be any chemical or biological species capable of providing or generating a nitro equivalent to be transferred to a compound, as described herein. In some cases, the analyte is a nitro-containing species. In some cases, the analyte is a non-aromatic, nitro-containing species. The analyte may be, for example, a nitramine-containing species or a nitroester-containing species. In some cases, the analyte may be an explosive. For example, the analyte may be RDX, DMNB, PETN, HMX, other nitro- or nitrate-containing species (e.g., nitroamines), and the like. In some embodiments, the analyte is RDX. In some embodiments, the analyte is PETN.

The analyte may be determined in either solution phase or in vapor phase. For example, a sample suspected of containing the analyte may be combined in solution with a compound as described herein. In some embodiments, a vapor sample suspected of containing the analyte may contacted with a film comprising a compound as described herein, or other solid comprising a compound as described herein.

Some embodiments may involve determination of analytes which may be present in the microgram scale. Other embodiments involve determination of analytes at lower concentrations, including analytes present in trace amounts. For example, a method may comprise exposure of a material as described herein to a sample suspected of containing an analyte on the microgram, nanogram, or picogram scale. In some embodiments, the analyte may be present in trace amounts. In an illustrative embodiment, the presence of approximately 100 pg of RDX or PETN in the solid state can be detected within one minute by the devices and methods described herein, upon exposure to sunlight.

As used herein, an emitted radiation or "emission" may be luminescence emission, in which "luminescence" is defined as an emission of ultraviolet or visible radiation. Specific types of luminescence include fluorescence; in which a time interval between absorption and emission of visible radiation ranges from $10^{-12}$ to $10^{-7}$ s, phosphorescence, other types of luminescence, and the like. For example, the emission may be "chemiluminescence," which refers to emission of radiation due to a chemical reaction, or "electrochemiluminescence," which refers to emission of radiation due to electrochemical reactions. In some cases, the emission may be fluorescence emission.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls have from about 3 to about 10 carbon atoms in their ring structure, and alternatively about 5, 6 or 7 carbons in the ring structure. Examples of alkyl groups include, but are not limited to, methyl, ethyl, n propyl, n butyl, n pentyl, n hexyl, n-heptyl, n-octyl, n-nonyl and n-decyl, isopropyl, sec butyl, isobutyl, tert butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

The term "heteroalkyl" is given its ordinary meaning in the art and refers to alkyl groups as described herein in which one or more atoms is a heteroatom (e.g., oxygen, nitrogen, sulfur, and the like). For example, an alkoxy group is a heteroalkyl group. Examples of heteroalkyl groups include, but are not limited to, alkoxy, amino, thioester, poly(ethylene glycol), and alkyl-substituted amino.

The term "alkenyl" refers to an alkyl group including at least one carbon-carbon double bond. Examples of alkenyl groups include, but are not limited to, vinyl, allyl, butenyl, pentenyl, and the like. The term "heteroalkenyl" and refers to alkenyl groups as described herein in which one or more atoms is a heteroatom (e.g., oxygen, nitrogen, sulfur, and the like).

The term "alkynyl" refers to an alkyl group including at least one carbon-carbon triple bond. Examples of alkynyl groups include, but are not limited to, acetylenyl, propynyl, butynyl, pentynyl, and the like. The term "heteroalkynyl" and refers to alkenyl groups as described herein in which one or more atoms is a heteroatom (e.g., nitrogen).

The term "aryl" is given its ordinary meaning in the art and refers to monocyclic aromatic group as well as polycyclic aromatic groups. The term "heteroaryl" is given its ordinary meaning in the art and refers to aryl groups as described herein in which one or more ring atoms is a heteroatom (e.g., oxygen, nitrogen, sulfur, and the like). Examples of aryl and heteroaryl groups include, but are not limited to, benzene, pyrrole, furan, thiophene, imidazole, oxazole, thiazole, triazole, pyrazole, pyridine, pyrazine, pyridazine, pyrimidine, naphthalene, anthracene, pyrene, and the like.

The term "heterocycle" refers to refer to cyclic groups containing at least one heteroatom as a ring atom, in some cases, 1 to 3 heteroatoms, as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures (e.g., 3- to 7-membered rings) whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, dihydroacridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle an optionally substituted dihydroacridine.

The term "polycyclic" refers to ring systems having two or more cyclic rings in which two or more atoms are common to two adjoining rings (e.g., the rings are "fused rings").

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted benzene" must still comprise the benzene moiety and can not be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, halo, nitro, cyano, lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, lower alkoxyalkyl, lower perhaloalkyl, lower arylalkyloxyalkyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

Materials, Instrumentation and General Experimental Methods. Synthetic manipulations that required an inert atmosphere (where noted) were carried out under argon using standard Schlenk techniques. All solvents were of reagent grade or better unless otherwise noted. All solvents used for photophysical experiments were of spectroscopic grade. Anhydrous tetrahydrofuran, diethyl ether, toluene and dichloromethane were obtained from a dry solvent system. Spectroscopic-grade acetonitrile was degassed and stored over 4 Å sieves. $^1$H and $^{13}$C NMR spectra for all compounds were acquired in CHCl$_3$ at 400 and 100 MHz, respectively. The chemical shift data are reported in units of δ (ppm) relative to tetramethylsilane (TMS) and referenced with residual CHCl$_3$. $^{19}$F NMR spectra were recorded at 380 MHz. Trichlorofluoromethane was used as an external standard (0 ppm) and upfield shifts are reported as negative values. In some cases, signals associated with the CF$_3$ groups and proximal quaternary centers were not reported in the $^{13}$C-NMR spectra due to C—F coupling and low signal-to-noise ratios. High-resolution mass spectra (HRMS) were obtained using a peak-matching protocol to determine the mass and error range of the molecular ion, employing either electron impact or electrospray as the ionization technique. GC-MS (electron impact mass spectrometer) data were recorded in the temperature range of 100-350° C. under a vacuum of at least 10$^{-5}$ torr. GC retention times are reported in minutes. X-ray crystal structures were determined with graphite-monochromated Mo Kα radiation (λ=0.71073 Å). All structures were solved by direct methods using SHELXS (see Sheldrick, G. M. *Acta Cryst. A* 1990, 46, 467, and Sheldrick, G. M. SHELXL 91, Universtität Göttingen, Göttingen, Germany, 1997) and refined against F on all data by full-matrix least squares with SHELXL-97. All non-hydrogen atoms were refined anisotropically. All electrochemical measurements were made using a quasi-internal Ag wire reference electrode submerged in 0.01 M AgNO$_3$/0.1 M n-Bu$_4$NPF$_6$ in anhydrous MeCN. Typical CVs were recorded using a platinum button electrode as the working electrode and a platinum coil counter electrode. The ferrocene/ferrocenium (Fc/Fc$^+$) redox couple was used as an external reference. Ultraviolet-visible absorption spectra were corrected for background signal with either a solvent-filled cuvette (solutions) or a blank microscope slide (films). Fluorescence spectra were measured using either right-angle (solutions) or front-face (22.5°) detection (thin films). Fluorescence quantum yields were determined by the optically dilute method described in Demas, J. N., Crosby, G. A. *J. Phys. Chem.* 1971, 75, 991, using quinine sulfate in 0.1M H$_2$SO$_4$ as a standard (Φ=0.53) and were corrected for solvent refractive index and absorption differences at the excitation wavelength. Fluorescence lifetimes were measured via frequency modulation using a 365 nm laser diode as the light source and the modulation of POPOP as a calibration reference. For photolysis experiments, solutions were irradiated under air at 313 nm using either: (1) the Xenon lamp (450 W) from a fluorimeter, with the excitation slit set to 29.4 nm (the maximum value); (2) a 500 W Mercury Arc Lamp fitted with a 313 nm interference filter (or a 334 nm or 365 nm interference filter) and varying neutral density filters (0.5, 1.0 or 2.0 OD); or (3) a solar simulator equipped with a 450 W Xenon arc lamp, with a spectral output of 1.3 suns under AM 1.5 conditions. For a representative reference on the procedure followed, see Hill, R. D.; Puddephatt, R. J. *J. Am. Chem. Soc.* 1985, 107, 1218. The first two light sources were calibrated with a potassium ferric oxalate actinometer (see Hatchard, C. G.; Parker, C. A. *Proc. R. Soc. London A* 1956, 235, 518). For each measurement, reaction progress was also monitored in the dark to ensure that there was no thermal contribution to the nitration of aromatic amines by RDX and PETN. Each photolysis experiment was performed in triplicate. N-Phenylanthranilic acid was esterified following the procedure described in Craig, D. *J. Am. Chem. Soc.* 1935, 57, 195. RDX and PETN were obtained from K-9 training units, which consisted of RDX/PETN adsorbed onto sand. RDX and PETN were extracted from the sand with spectral grade acetonitrile and precipitated by the addition of DI water. The solids thus isolated were recrystallized three times from chloroform/acetonitrile and stored in the dark at −4° C.

Example 1

Synthesis of N,N-Dimethyl-4-nitroaniline (DMNA)

A mixture of 0.4 mL DMA and 0.1 g of either RDX or PETN were dissolved in 3.0 mL dry, degassed acetonitrile and the solution photolyzed with a xenon arc lamp at 313 nm for 60 minutes. The reaction mixture was sampled every 10 minutes to determine the GC yield of the DMNA product. Approximately 80% of DMNA (GC yield) was formed after 60 minutes of photolysis. The yellow DMNA was isolated by flash column chromatography using 50/50 hexanes/dichloromethane as an eluent. $^1$H NMR (400 MHz, CHCl$_3$) δ 3.11 (s, 6H), 6.59 (d, J=8.2 Hz, 2H), 8.09 (d, J=8.2 Hz, 2H). $^{13}$C NMR (100 MHz, CHCl$_3$) δ 40.2, 110.2, 126.0, 136.9, 154.3. HRMS (ESI) calc for C$_8$H$_{11}$N$_2$O$_2$ [M+H]$^+$ 167.0815, found 167.0819. IR (KBr plate) 695 (s), 750 (s), 820 (s), 1067 (m), 1118 (m), 1232 (m), 1347 (m), 1383 (w), 1456 (s), 1483 (s), 1582 (s), 1615 (w), 2924 (m) cm$^{-1}$.

Example 2

General procedure for the synthesis of 9,9-disubstituted-9,10-dihydroacridines (DHA1-4).

A flame-dried Schlenk flask was charged with 1.0 g methyl N-phenylanthranilate (14, 4.4 mmol) and 45 mL dry, degassed Et$_2$O under argon and cooled to 0° C. in an ice bath. 3.5 Equivalents of the appropriate Grignard reagent in Et$_2$O were added dropwise and the reaction allowed to stir at room temperature under argon for 3 d. After quenching with saturated ammonium chloride, the organic layer was separated, washed with brine and water and dried over MgSO$_4$, and the solvent evaporated under reduced pressure. The crude tertiary alcohol thus formed was carried on to the next step without purification. To the neat oil isolated from the previous step was added 1-2 mL of concentrated H$_2$SO$_4$ under argon and the reaction stirred at room temperature for 1 h under argon. After dilution with 30 mL DI H$_2$O the reaction was poured into a 10% (v/v) aqueous ammoniacal solution and extracted with ether (5×50 mL). The combined organic layers were washed with saturated sodium bicarbonate, brine and water and dried over MgSO$_4$, and the solvent evaporated under reduced pressure. The residue was purified by flash column chromatography to yield the desired compound.

Example 3

Synthesis of 9,9-Dimethyl-9,10-dihydroacridine (DHA1)

The title compound was synthesized using 3.0 M methyl magnesium bromide in Et$_2$O and purified by flash column chromatography using gradient elution, starting with 10% dichloromethane in hexanes and progressing to 50% dichloromethane in hexanes. 0.41 g (45%) of a white solid was isolated. m.p. 120° C. $^1$H NMR (400 MHz, CHCl$_3$) δ 1.54 (s, 6H), 6.11 (s, 1H), 6.67 (dd, J=0.8 Hz, 7.6 Hz, 2H), 6.90 (m, 2H), 7.09 (m, 2H), 7.37 (d, J=7.6 Hz, 2H). $^{13}$C NMR (100 MHz, CHCl$_3$) δ 30.7, 36.4, 113.6, 120.8, 125.7, 126.9, 129.3, 138.6. HRMS (ESI) calc for C$_{15}$H$_{15}$N [M+H]$^+$ 210.1277, found 210.1284. IR (KBr plate) 745 (s), 886 (m), 1037 (m), 1318 (m), 1452 (m), 1479 (s), 1507 (m), 1580 (m), 1606 (m), 2966 (m), 3359 (m) cm$^-$.

Example 4

Synthesis of 9,9-Diethyl-9,10-dihydroacridine (DHA2)

The title compound was synthesized using 3.0 M ethyl magnesium bromide in Et$_2$O and purified by flash column chromatography using hexanes as the eluent. 0.36 g (35%) of a clear oil was isolated.$^1$H NMR (400 MHz, CHCl$_3$) δ 0.91 (t, J=7.6 Hz, 3H), 0.97 (t, J=7.6 Hz, 3H), 2.24 (q, J=7.6 Hz, 2H), 2.35 (q, J=7.6 Hz, 2H), 5.74 (s, 1H), 6.90 (m, 3H), 7.06 (m, 5H). $^{13}$C NMR (100 MHz, CHCl$_3$) δ 13.0, 13.1, 13.9, 14.8, 24.3, 31.7, 115.9, 116.8, 118.2, 118.5, 120.3, 120.5, 121.0, 121.2, 123.0, 124.9, 127.4, 127.5, 129.5, 129.7, 130.1, 130.2, 134.3, 140.1, 140.3, 141.2, 143.5, 143.7. HRMS (ESI) calc for C$_{17}$H$_{19}$N [M+H]$^+$ 238.1590, found 238.1591. IR (KBr plate) 692 (m), 745 (s), 1309 (m), 1451 (m), 1507 (s), 1575 (m), 1593 (s), 2871 (m), 2930 (m), 2965 (m), 3041 (m), 3403 (m) cm$^{-1}$.

Example 5

Synthesis of 9,9-Diisopropyl-9,10-dihydroacridine (DHA3)

The title compound was synthesized using 2.0 M isopropyl magnesium chloride in Et$_2$O and purified by flash column chromatography using hexanes as the eluent. 0.19 g (17%) of a clear oil was isolated. $^1$H NMR (400 MHz, CHCl$_3$) δ 0.77 (d, J=6.8 Hz, 3H), 1.02 (d, J=6.8 Hz, 3H), 1.46 (s, 3H), 1.87 (s, 3H), 3.06 (septet, J=6.8 Hz, 1H), 5.75 (s, 1H), 6.88 (m, 5H), 7.20 (m, 4H). $^{13}$C NMR (100 MHz, CHCl$_3$) δ 19.7, 20.9, 22.4, 22.2, 30.6, 115.5, 118.6, 119.8, 121.2, 127.1, 129.5, 129.8, 130.0, 130.7, 136.8, 141.0, 143.5. HRMS (ESI) calc for C$_{19}$H$_{24}$N [M+H]$^+$ 266.1903, found 266.1904. IR (KBr plate) 693 (s), 745 (s), 1079 (m), 1309 (s), 1450 (s), 1508 (s), 1576 (s), 1594 (s), 2961 (m), 3399 (s) cm$^{-1}$.

Example 6

Synthesis of 9,9-Diphenyl-9,10-dihydroacridine (DHA4)

The title compound was synthesized using 3.0 M phenyl magnesium bromide in Et$_2$O and purified by flash column chromatography using gradient elution, starting with 10% dichloromethane in hexanes and progressing to 50% dichloromethane in hexanes. 0.83 g (57%) of a white solid was isolated. m.p. 230° C. $^1$H NMR (400 MHz, CHCl$_3$) δ 6.25 (s, 1H), 6.86 (m, 9H), 7.16 (m, 8H). $^{13}$C NMR (100 MHz, CHCl$_3$) δ 30.1, 56.7, 113.5, 120.2, 125.6, 126.1, 126.2, 127.1, 127.4, 127.6, 127.6, 127.9, 128.5, 130.0, 130.2, 130.2, 139.7, 146.0, 149.3. HRMS (ESI) calc for C$_{25}$H$_{19}$N [M+H]$^+$ 334.1590, found 334.1584. IR (KBr plate) 699 (m), 734 (m), 753 (m), 907 (m), 1315 (m), 1474 (s), 1604 (m), 3057 (w), 3393 (m) cm$^{-1}$.

Example 7

Synthesis of Methyl N-methyl-N-phenylanthranilate (15)

A flame-dried two-neck round bottom flask was charged with 8 g N-phenylanthranilic acid (37.5 mmol), 0.3 mL 15-crown-5, 300 mL dry THF and 100 mL dimethoxyethane under argon. The solution was cooled to 0° C. in an ice bath, 5 g of a 60 wt % dispersion of NaH in mineral oil (3 g NaH, 125 mmol) was added to the reaction mixture in small portions under argon and 15 mL dimethyl sulfate (19.99 g, 158 mmol) was added via syringe. After stirring at room temperature for 5 d under argon the reaction was poured carefully onto 800 g ice and extracted with Et$_2$O (5×50 mL). The organic layers were combined, washed thoroughly with saturated sodium bicarbonate (3×25 mL), brine and water, dried over MgSO$_4$ and the solvent evaporated under reduced pressure. The resulting oil was purified by flash column chromatography using gradient elution, starting with 100% hexanes and progressing to 30% dichloromethane in hexanes to yield 7.2 g (80%) of a yellow oil. $^1$H NMR (400 MHz, CHCl$_3$) δ 3.28

(s, 3H), 3.58 (s, 3H), 6.63 (dd, J=8.8 Hz, J=1.2 Hz, 2H), 6.73 (td, , J=6 Hz, J=1.2 Hz, 1H), 7.16 (td, J=7.2 Hz, J=1.6 Hz, 2H), 7.27 (m, 2H), 7.53 (td, J=8 Hz, J=1.6 Hz, 1H), 7.79 (dd, J=7.6 Hz, J=1.6 Hz, 1H). $^{13}$C NMR (100 MHz, CHCl$_3$) δ 40.5, 52.3, 114.4, 118.1, 125.4, 129.1, 129.2, 129.4, 131.6, 133.4, 148.3, 129.4, 167.7. HRMS (ESI) calc for C$_{15}$H$_{15}$NO$_2$ [M+H]$^+$ 242.1176, found 242.1170. IR (KBr plate) 2924 (s), 2853 (s), 1728 (m), 1594 (m), 1500 (m), 1454 (m), 1391 (w), 1253 (s), 1214 (s), 1062 (m), 1005 (m), 758 (m), 575 (m) cm$^{-1}$.

Example 7

The following example describes the general procedure for the synthesis of 9,9-disubstituted-10-methyl-9,10-dilydroacridines (DHA5-9). A flame-dried Schlenk flask was charged with 1.0 g methyl N-methyl-N-phenylanthranilate (15, 4.1 mmol) and 45 mL dry, degassed Et$_2$O under argon and cooled to 0° C. in an ice bath. 2.5 Equivalents of the appropriate Grignard reagent in Et$_2$O was added dropwise and the reaction allowed to stir at room temperature under argon for 3 d. After quenching with saturated ammonium chloride, the organic layer was separated, washed with brine and water and dried over MgSO$_4$, and the solvent evaporated under reduced pressure. The crude tertiary alcohol thus formed was carried on to the next step without purification. To the neat oil isolated from the previous step was added 1-2 mL of concentrated H$_2$SO$_4$ under argon and the reaction stirred at room temperature for 1 h under argon. After dilution with 30 mL DI H$_2$O the reaction was poured into a 10% (v/v) aqueous ammoniacal solution and extracted with ether (5×50 mL). The combined organic layers were washed with saturated sodium bicarbonate, brine and water and dried over MgSO$_4$, and the solvent evaporated under reduced pressure. The residue was purified by flash column chromatography to yield the desired compound.

Example 8

Synthesis of
9,9-Dimethyl-10-methyl-9,10-dihydroacridine
(DHA5)

The title compound was synthesized using 3.0 M methyl magnesium bromide in Et$_2$O and purified by flash column chromatography using gradient elution, starting with 10% dichloromethane in hexanes and progressing to 50% dichloromethane in hexanes. 0.39 g (42%) of a light yellow solid was isolated. m.p. 93° C. $^1$H NMR (400 MHz, CHCl$_3$) δ 1.52 (s, 6H), 3.43 (s, 3H), 6.96 (m, 4H), 7.21 (m, 2H), 7.38 (d, J=1.6 Hz, 2H).
$^{13}$C NMR (100 MHz, CHCl$_3$) δ 27.4, 33.5, 36.7, 112.3, 120.8, 123.8, 126.8, 132.8, 142.4. HRMS (ESI) calc for C$_{16}$H$_{17}$N [M+H]$^+$ 224.1434, found 224.1429. IR (KBr plate) 751 (s), 1046 (m), 1268 (s), 1340 (s), 1450 (s), 1470 (s), 1590 (s), 2900 (m), 2950 (s), 2980 (s), 3050 (m) cm$^{-1}$.

Example 9

Synthesis of
9,9-Diethyl-10-methyl-9,10-dihydroacridine
(DHA6)

The title compound was synthesized using 3.0 M ethyl magnesium bromide in Et$_2$O and purified by flash column chromatography using hexanes as the eluent. 0.31 g (30%) of a clear oil was isolated. $^1$H NMR (400 MHz, CHCl$_3$) δ 0.81 (t, J=7.6 Hz, 3H), 0.84 (t, J=7.6 Hz, 3H), 2.14 (q, J=7.6 Hz, 2H), 2.27 (q, J=7.6 Hz, 2H), 3.06 (s, 3H), 6.65 (m, 3H), 7.17 (m, 5H). $^{13}$C NMR (100 MHz, CHCl$_3$) δ 14.2 (2), 14.3, 22.5, 22.8, 23.2, 23.4, 29.6, 30.4, 31.0, 31.2, 31.7, 37.1, 39.4, 39.6, 114.0, 114.1, 117.2, 117.3, 125.5, 125.9, 127.8, 128.1, 128.2, 128.4, 128.7, 128.9, 130.5, 132.0, 132.5, 140.0, 140.1, 141.5, 143.4, 146.1, 147.0, 149.3, 149.5. HRMS (ESI) calc for C$_{18}$H$_{21}$N [M+H]$^+$ 252.1747, found 252.1742. IR (KBr plate) 692 (s), (748 (s), 1342 (m), 1444 (m), 1487 (s), 1500 (s), 1568 (m), 1592 (s), 1602 (s), 2810 (m), 2870 (m), 2963 (m), 3024 (m) cm$^{-1}$.

Example 10

Synthesis of
9,9-Diisopropyl-10-methyl-9,10-dihydroacridine
(DHA7)

The title compound was synthesized using 2.0 M isopropyl magnesium chloride in Et$_2$O and purified by flash column chromatography using hexanes as the eluent. 0.19 g (17%) of a clear oil was isolated. $^1$H NMR (400 MHz, CHCl$_3$) δ 0.85 (d, J=7.2 Hz, 3H), 0.89 (d, J=7.6 Hz, 3H), 1.46 (s, 3H), 1.80 (s, 3H), 2.84 (septet, J=7.2 Hz, 1H), 3.03 (s, 3H), 6.74 (m, 3H), 6.98 (m, 1H), 7.13 (m, 5H). $^{13}$C NMR (100 MHz, CHCl$_3$) δ 21.6, 22.3, 23.8, 31.8, 39.0, 114.6, 117.4, 120.6, 121.4, 125.2, 127.4, 127.8, 128.0, 128.7, 129.4, 133.6, 140.0, 141.2, 147.2, 149.6. HRMS (ESI) calc for C$_{20}$H$_{25}$N [M+H]$^+$ 280.2060, found 280.2058. IR (KBr plate) 748 (m), 1499 (m), 1601 (m), 2820 (m), 2910 (m) 3040 (m) cm$^{-1}$.

Example 11

Synthesis of
9,9-Diphenyl-10-methyl-9,10-dihydroacridine
(DHA8)

The title compound was synthesized using 3.0 M phenyl magnesium bromide in Et$_2$O and purified by flash column chromatography using gradient elution, starting with 10% dichloromethane in hexanes and progressing to 50% dichloromethane in hexanes. 0.79 g (55%) of a light yellow solid was isolated. m.p. 165-166° C. $^1$H NMR (400 MHz, CHCl$_3$) δ 3.29 (s, 3H), 6.84 (m, 2H), 6.91 (m, 8H), 7.18 (m, 6H), 7.26 (m, 2H). $^{13}$C NMR (100 MHz, CHCl$_3$) δ 33.6, 57.3, 112.1, 120.0, 126.4, 127.4, 127.7, 130.1, 130.6, 131.4, 142.7, 146.2. HRMS (ESI) calc for C$_{26}$H$_{21}$N [M+H]$^+$ 348.1747, found 348.1732. IR (KBr plate) 638 (m), 699 (m), 733 (m), 755 (m), 1270 (m), 1348 (m), 1468 (s), 1590 (m), 1589 (m), 2815 (w), 2873 (w), 3056 (m) cm$^{-1}$.

Example 12

Synthesis of
9,9-Di-n-octyl-10-methyl-9,10-dihydroacridine
(DHA9)

The title compound was synthesized using 2.0 M octyl magnesium bromide in Et$_2$O and purified by flash column chromatography using hexanes as the eluent. 0.7 g (40%) of a clear oil was isolated. $^1$H NMR (400 MHz, CHCl$_3$) δ 0.85 (t, J=7.6 Hz, 3H), 0.88 (t, J=7.2 Hz, 3H), 1.22 (bm, 22H), 2.08 (q, J=7.2 Hz, 2H), 2.25 (t, J=7.6 Hz, 2H), two overlapping singlets: δ 3.08, 3.10, total 3H, 5.35 (t, J=7.6 Hz, 1H), 6.67 (m, 3H), 7.17 (m, 6H). $^{13}$C NMR (100 MHz, CHCl$_3$) δ 14.4, 22.9 (3), 28.3, 28.7, 29.0, 29.3, 29.5 (2), 29.6, 29.7 (2), 29.8, 30.0, 30.3, 31.1, 32.1 (2), 37.4, 39.4, 39.6, 114.0, 114.1, 117.2, 117.3, 125.5, 125.9, 128.0 (2), 128.2, 128.4, 128.6, 128.9, 130.7, 132.0, 132.5, 140.0, 140.7, 141.3, 143.4, 146.1, 146.9, 149.3, 149.5. HRMS (ESI) calc for $C_{30}H_{45}N$ $[M+H]^+$ 420.3625, found 420.3613. IR (KBr plate) 692 (m), 747 (m), 1095 (w), 1342 (m), 1499 (s), 1592 (s), 1602 (s), 2854 (s), 2924 (s), 2955 (s), 3024 (w) $cm^{-1}$.

Example 13

Synthesis of 2-Bromo-N-methyl-N-phenylaniline (18)

A flame-dried two-neck round bottom flask was charged with 2-bromo-N-phenylaniline (3 g, 12.2 mmol), 0.1 mL 15-crown-5, 200 mL dry THF and 50 mL dimethoxyethane under argon. The solution was cooled to 0° C. in an ice bath, 0.6 g of a 60 wt % dispersion of NaH in mineral oil (0.36 g NaH, 15 mmol) was added to the reaction mixture in small portions under argon and 1.4 mL dimethyl sulfate (1.89 g, 15 mmol) was added via syringe. After refluxing for 20 h under argon the reaction was poured carefully onto 500 g ice and extracted with $Et_2O$ (5×50 mL). The organic layers were combined, washed thoroughly with saturated sodium bicarbonate (3×25 mL), brine and water, dried over $MgSO_4$ and the solvent evaporated under reduced pressure. The resulting oil was purified by flash column chromatography using gradient elution, starting with 100% hexanes and progressing to 30% dichloromethane in hexanes to yield 2.5 g (80%)-of a clear oil. $^1$H NMR (400 MHz, $CHCl_3$) δ 3.22 (s, 3H), 6.56 (d, J=7.6 Hz, 2H), 6.75 (t, J=7.6 Hz, 1H), 7.15 (m, 3H), 7.25 (dd, J=8.0 Hz, J=2.0 Hz, 1H), 7.32 (td, J=7.6 Hz, J=1.2 Hz, 1H), 7.66 (dd, J=8.0 Hz, J=1.6 Hz, 1H). $^{13}$C NMR (100 MHz, $CHCl_3$) δ 39.1, 113.5, 117.8, 124.4, 127.9, 128.4, 129.1, 129.2, 130.6, 134.3, 147.0, 148.7. HRMS (ESI) calc for $C_{13}H_{12}BrN$ $[M+H]^+$ 262.0226, found 262.0234. IR (KBr plate) 654 (s), 691 (s), 748 (s), 872 (s), 1139 (s), 1137 (s), 1273 (s), 1346 (s), 1438 (m), 1467 (s), 1499 (s), 1580 (s), 1601 (s), 2813 (m), 2824 (s), 3058 (m), 3089 (m) $cm^{-1}$.

Example 14

Synthesis of 9-Ethyl-9,10-dimethyl-9,10-dihydroacridine (DHA10)

A flame-dried two-necked flask was charged with 2-bromo-N-methyl-N-phenylaniline (1.0 g, 3.8 mmol) and 100 mL dry THF under argon and cooled to −78° C. in a dry ice-acetone bath. 2.6 mL of a 1.6 M solution of n-BuLi in hexanes (4.16 mmol) was added dropwise over 5 minutes and the reaction stirred at −78° C. under argon for 1 h. Methyl ethyl ketone (0.302 g, 4.2 mmol) was added in one portion to the reaction mixture at −78° C., the reaction allowed to warm to room temperature and stirred overnight under argon. After quenching with saturated ammonium chloride, the reaction was extracted with $Et_2O$, the organic layers combined, washed with brine and water and dried over anhydrous $MgSO_4$ and the solvent evaporated under reduced pressure. To the neat residue thus obtained was added 2 mL of concentrated $H_2SO_4$ under argon and the mixture stirred at room temperature for 1 h under argon. After dilution with 30 mL DI $H_2O$, the reaction was extracted with $Et_2O$ (5×50 mL), the organic layers were combined, washed with brine and water and dried over anhydrous $MgSO_4$, and the solvent was evaporated under reduced pressure. The residue was purified by flash column chromatography using hexanes as the eluent to yield 0.57 g (57%) of the desired compound as a clear oil. $^1$H NMR (400 MHz, $CHCl_3$) δ 1.66 (dd, J=6.8 Hz, J=0.8 Hz, 3H), 1.78 (t, J=1.2 Hz, 3H), 3.10 (s, 3H), 5.49 (m, 1H), 6.66 (m, 3H), 7.18 (m, 6H). $^{13}$C NMR (100 MHz, $CHCl_3$) δ 14.2, 15.2, 16.5, 24.2, 39.2, 39.6, 113.8, 114.1, 117.1, 117.4, 122.4, 124.4, 125.7025.9, 128.0, 128.2, 128.5, 128.8, 128.9, 130.6, 131.5, 136.4, 140.4, 144.3, 145.8, 146.9, 149.2, 149.4. HRMS (ESI) calc for $C_{17}H_{19}N$ $[M+H]^+$ 238.1590, found 238.1587. IR (KBr plate) 692 (m), 747 (m), 1345 (m), 1444 (m), 1499 (s), 1592 (s), 1602 (s), 2918 (m), 3024 (m) $cm^{-1}$.

Example 15

Synthesis of 9-Methyl-9-phenyl-10-methyl-9,10-dihydroacridine (DHA11)

A flame-dried two-necked flask was charged with 2-bromo-N-methyl-N-phenylaniline (1.0 g, 3.8 mmol) and 100 mL dry THF under argon and cooled to −78° C. in a dry ice-acetone bath. 2.6 mL of a 1.6 M solution of n-BuLi in hexanes (4.16 mmol) was added dropwise over 5 minutes and the reaction stirred at −78° C. under argon for 1 h. Acetophenone (0.49 mL, 0.51 g, 4.2 mmol) was added in one portion under argon at −78° C., the reaction allowed to warm to room temperature and stirred overnight under argon. After quenching with saturated ammonium chloride, the reaction was extracted with $Et_2O$, the organic layers combined, washed with brine and water and dried over anhydrous $MgSO_4$ and the solvent evaporated under reduced pressure. To the neat residue thus obtained was added 2 mL of concentrated $H_2SO_4$ under argon and the mixture stirred at room temperature for 1 h under argon. After dilution with 30 mL DI $H_2O$, the reaction was extracted with $Et_2O$ (5×50 mL), the organic layers were combined, washed with brine and water and dried over anhydrous $MgSO_4$, and the solvent was evaporated under reduced pressure. The desired product was purified by flash column chromatography using gradient elution, starting with 20% dichloromethane in hexanes and progressing to 50% dichloromethane in hexanes to yield 0.55 g (50%) of a light yellow solid. m.p. 184° C. $^1$H NMR (400 MHz, $CHCl_3$) δ 1.83 (s, 3H), 3.37 (s, 3H), 6.93 (m, 6H), 7.24 (m, 8H). $^{13}$C NMR (100 MHz, $CHCl_3$) δ 27.4, 28.2, 31.2, 33.6, 112.1 (2), 112.3, 113.7, 113.9, 116.9, 120.0, 120.4, 120.8, 123.8, 126.2, 126.4, 126.76, 126.7, 127.1, 127.38, 127.5, 127.7, 127.8, 127.9, 128.0, 128.5, 128.7, 128.8, 128.9, 130.1, 130.5, 131.4, 132.5, 142.0, 142.7, 146.2, 148.9. HRMS (ESI) calc for $C_{21}H_{19}N$ $[M+H]^+$ 286.1590, found 286.1590. IR (KBr plate) 650 (m), 699 (m), 743 (m), 798 (m), 1290 (m), 1353 (m), 1468 (s), 1595 (m), 1631 (m), 2803 (w), 2898 (w), 3042 (m) $cm^{-1}$.

Example 16

Synthesis of 9-Isopropyl-9,10-dimethyl-9,10-dihydroacridine (DHA12)

A flame-dried two-necked flask was charged with 2-bromo-N-methyl-N-phenylaniline (1.0 g, 3.8 mmol) and 100 mL dry THF under argon and cooled to −78° C. in a dry ice-acetone bath. 2.6 mL of a 1.6 M solution of n-BuLi in hexanes (4.16 mmol) was added dropwise over 5 minutes and the reaction stirred at −78° C. under argon for 1 h. Isopropyl methyl ketone (0.361 g, 4.2 mmol) was added in one portion to the reaction mixture at −78° C., the reaction allowed to warm to room temperature and stirred overnight under argon. After quenching with saturated ammonium chloride, the reaction was extracted with $Et_2O$, the organic layers combined, washed with brine and water and dried over anhydrous MgSO$_4$ and the solvent evaporated under reduced pressure. To the neat residue thus obtained was added 2 mL of concentrated H$_2$SO$_4$ under argon and the mixture stirred at room temperature for 1 h under argon. After dilution with 30 mL DI H$_2$O, the reaction was extracted with Et$_2$O (5×50 mL), the organic layers were combined, washed with brine and water and dried over anhydrous MgSO$_4$, and the solvent was evaporated under reduced pressure. The residue was purified by flash column chromatography using hexanes as the eluent to yield 0.62 g (60%) of the desired compound as a clear oil. $^1$H NMR (400 MHz, CHCl$_3$) δ 1.51 (s, 3H), 1.64 (s, 3H), 1.70 (s, 3H), 3.04 (s, 3H), 6.64 (m, 3H), 7.12 (m, 6H). $^{13}$C NMR (100 MHz, CHCl$_3$) δ 21.5, 22.2, 23.8, 31.8, 39.0, 114.6, 117.4, 120.6, 121.4, 125.1, 127.4, 127.8, 128.0, 128.7, 129.3, 133.6, 140.0, 141.1, 147.2, 149.5. HRMS (ESI) calc for C$_{18}$H$_{21}$N [M+H]$^+$ 252.1747, found 252.1742. IR (KBr plate) 692 (m), 747 (s), 1137 (m), 1342 (m), 1443 (m), 1486 (s), 1499 (s), 1591 (s), 1601 (s), 2911 (m), 2984 (m) cm$^{-1}$.

Example 17

Synthesis of
9-Ethyl-9-phenyl-10-methyl-9,10-dihydroacridine
(DHA13)

A flame-dried two-necked flask was charged with 2-bromo-N-methyl-N-phenylaniline (1.0 g, 3.8 mmol) and 100 mL dry THF under argon and cooled to −78° C. in a dry ice-acetone bath. 2.6 mL of a 1.6 M solution of n-BuLi in hexanes (4.16 mmol) was added dropwise over 5 minutes and the reaction stirred at −78° C. under argon for 1 h. Propiophenone (0.56 mL, 0.56 g, 4.2 mmol) was added in one portion to the reaction mixture under argon at −78° C., the reaction allowed to warm to room temperature and stirred overnight under argon. After quenching with saturated ammonium chloride, the reaction was extracted with Et$_2$O, the organic layers combined, washed with brine and water and dried over anhydrous MgSO$_4$ and the solvent evaporated under reduced pressure. To the neat residue thus obtained was added 2 mL of concentrated H$_2$SO$_4$ under argon and the mixture stirred at room temperature for 1 h under argon. After dilution with 30 mL DI H$_2$O, the reaction was extracted with Et$_2$O (5×50 mL), the organic layers were combined, washed with brine and water and dried over anhydrous MgSO$_4$, and the solvent was evaporated under reduced pressure. The desired product was purified by flash column chromatography using 10% dichloromethane in hexanes as the eluent to yield 0.62 g (55%) of a light yellow oil. $^1$H NMR (400 MHz, CHCl$_3$) δ 0.74 (t, J=7.2 Hz, 3H), 2.22 (q, J=7.2 Hz, 2H), 3.38 (s, 3H), 6.75 (m, 4H), 6.89 (m, 2H), 7.17 (m, 3H), 7.27 (m, 4H). $^{13}$C NMR (100 MHz, CHCl$_3$) δ 9.7, 33.8, 34.6, 50.5, 111.9, 113.1, 113.8, 114.0, 116.9, 119.9, 125.4, 125.6, 125.9, 126.4, 126.5, 126.6, 126.7, 127.0, 127.3, 127.5, 127.8, 127.9, 128.2, 128.3, 128.8, 128.9, 129.2, 129.4, 129.6, 130.2, 132.9, 138.7, 141.3, 142.0, 143.5, 147.3, 148.5, 149.5. HRMS (EI) calc for C$_{22}$H$_{21}$N [M]$^+$ 299.1669, found 299.1673. IR (KBr plate) 633 (m), 693 (s), 747 (s), 1032 (w), 1260 (w), 1349 (m), 1448 (m), 1499 (s), 1575 (m), 1590 (s), 1601 (s), 2927 (m), 3024 (m) cm$^{-1}$.

Example 18

Synthesis of 10-methyl-10H-spiro[acridine-9,1'-cyclohexane] (DHA14)

A flame-dried two-necked flask was charged with 2-bromo-N-methyl-N-phenylaniline (1.0 g, 3.8 mmol) and 100 mL dry THF under argon and cooled to −78° C. in a dry ice-acetone bath. 2.6 mL of a 1.6 M solution of n-BuLi in hexanes (4.16 mmol) was added dropwise over 5 minutes and the reaction stirred at −78° C. under argon for 1 h. Cyclohexanone (0.43 mL, 0.412 g, 4.2 mmol) was added in one portion to the reaction mixture at −78° C., the reaction allowed to warm to room temperature and stirred overnight under argon. After quenching with saturated ammonium chloride, the reaction was extracted with Et$_2$O, the organic layers combined, washed with brine and water and dried over anhydrous MgSO$_4$ and the solvent evaporated under reduced pressure. To the neat residue thus obtained was added 2 mL of concentrated H$_2$SO$_4$ under argon and the mixture stirred at room temperature for 1 h under argon. After dilution with 30 mL DI H$_2$O, the reaction was extracted with Et$_2$O (5×50 mL), the organic layers were combined, washed with brine and water and dried over anhydrous MgSO$_4$, and the solvent was evaporated under reduced pressure. The residue was purified by flash column chromatography using hexanes as the eluent to yield 0.3 g (30%) of the desired compound as a clear oil. $^1$H NMR (400 MHz, CHCl$_3$) δ 1.53 (m, 4H), 2.10 (m, 4H), 3.12 (s, 3H), 5.65 (m, 1H), 6.66 (m, 3H), 7.18 (m, 6H). $^{13}$C NMR (100 MHz, CHCl$_3$) δ 22.0, 23.0, 25.6, 28.2, 39.2, 113.7, 116.9, 125.6, 126.3, 127.7, 128.2, 128.5, 130.3, 137.9, 142.8, 145.6, 149.0. HRMS (ESI) calc for C$_{19}$H$_{21}$N [M+H]$^+$ 264.1747, found 264.1758. IR (KBr plate) 693 (m), 747(m), 1069 (s), 1155 (m), 1263 (m), 1345 (m), 1499 (s), 1602(s), 2853 (m), 2921 (s) cm$^{-1}$.

Example 19

Synthesis of 1,1,1,3,3,3-hexafluoro-2-(2-(methyl(phenyl)amino)phenyl)propan-2-ol (21)

A flame-dried two-necked flask equipped with a dry ice/acetone condenser was charged with 2-bromo-N-methyl-N-phenylaniline (1.0 g, 3.8 mmol) and 100 mL dry THF under argon and cooled to −78° C. in a dry ice-acetone bath. 2.6 mL of a 1.6 M solution of n-BuLi in hexanes (4.16 mmol) was added dropwise over 5 minutes and the reaction stirred at −78° C. under argon for 1 h. Making sure that the dry ice/acetone condenser remained filled, anhydrous hexafluoroacetone (HFA) gas was bubbled into the reaction flask at −78° C. under a positive pressure of argon for a total duration of 3 minutes; the pressure reading on the HFA tank was noted to be 22 psi. The reaction was allowed to warm to room temperature and the HFA allowed to reflux for an additional 3 h (making sure the dry ice/acetone condenser remained full for the duration) after which the excess HFA was removed by bubbling through a saturated KOH solution for 1 h. The reaction was quenched with saturated ammonium chloride and extracted with Et$_2$O (3×50 mL). The organic layers were combined, washed with brine and water and dried over MgSO$_4$, and the solvent was evaporated under reduced pressure. The residue was purified by flash column chromatography using 50% dichloromethane in hexanes as the eluent to yield g 1.1 g (80%) of the desired compound as a white crystalline solid after drying in vacuo for 3 d. $^1$H NMR (400 MHz, CHCl$_3$) δ 3.08 (s, 3H), 6.87 (dd, J=8.0 Hz, J=1.6 Hz, 2H), 6.98 (m, 2H), 7.21 (m, 2H), 7.36 (m, 2H), 7.75 (d, J=8.0 Hz, 1H), 11.51 (s, 1H). $^{13}$C NMR (100 MHz, CHCl$_3$) δ 40.3, 80.3 (quintet), 115.0, 115.5, 118.8, 119.2 (2), 119.4, 120.6 121.5, 121.6, 122.0, 122.1, 122.9, 124.9 (3), 127.2, 127.7, 127.8, 127.9, 128.3, 128.9 (2), 129.0, 129.2, 129.3, 129.4, 129.6, 132.3, 149.2, 151.6. $^{19}$F NMR (380 MHz, CHCl$_3$) δ −76.4, −75.1. HRMS (ESI) calc for C$_{16}$H$_{13}$F$_6$NO [M+H]$^+$ 350.0974, found 350.0961. IR (KBr plate) 479 (m), 693 (s), 709 (s), 754 (s), 848 (m), 936 (m), 954 (s), 968 (s), 1121 (s), 1147 (m), 1192 (s), 1260 (s), 1496 (s), 1577 (m), 1603 (m), 2719 (m), 2973 (m), 3066 (m), 3854 (broad) cm$^{-1}$.

Example 20

Synthesis of 10-methyl-9,9-bis(trifluoromethyl)-9, 10-dihydroacridine (DHA15)

1,1,1,3,3,3-hexafluoro-2-(2-(methyl(phenyl)amino)phenyl)propan-2-ol (0.2 g, 0.57 mmol) was dissolved in 15 mL POCl$_3$ and the solution refluxed under argon for 3 d. Excess POCl$_3$ was distilled off using a short path distillation head, the residue was dissolved in CHCl$_3$, poured into a 10% (v/v) aqueous ammoniacal solution and the biphasic system stirred at room temperature for one hour. The organic layer was separated and the aqueous layer extracted with Et$_2$O (3×50 mL). The organic layers were combined, washed with brine and water and dried over MgSO$_4$, and the solvent evaporated under reduced pressure. The residue was purified by flash column chromatography using 10% dichloromethane in hexanes as the eluent to yield 0.15 g (80%) of the desired compound as a light-blue oil. $^1$H NMR (400 MHz, CHCl$_3$) δ 3.46 (s, 3H), 7.00 (m, 4H), 7.42 (m, 2H), 7.89 (m, 2H). $^{13}$C NMR (100 MHz, CHCl$_3$) δ 29.8, 35.1, 111.8, 114.7, 120.3, 130.3 (quintet), 130.7, 141.8. $^{19}$F NMR (380 MHz, CHCl$_3$) δ −65.9. HRMS (EI) calc for C$_{16}$H$_{11}$F$_6$N [M]$^+$ 332.0868, found 332.0874. IR (KBr plate) 479 (m), 693 (s), 709 (s), 758 (s), 848 (m), 954 (s), 1116 (s), 1163 (m), 1192 (s), 1260 (s), 1489 (s), 1573 (m), 1594 (m), 2840 (m), 2972 (m), 3054 (m) cm$^{-1}$.

Example 21

Synthesis of Methyl N-(p-tolyl)-N-phenylanthranilate (22)

A flame-dried Schlenk flask was charged with 14 (5 g, 22 mmol), 4-bromotoluene (3 mL, 4.17 g, 24 mmol), copper powder (1.56 g, 24 mmol), copper (I) iodide (100 mg), potassium carbonate (3.3 g, 24 mmol), and 5 mL hexyl ether under argon. The resulting mixture was heated to 190° C. in a sand bath for 24 h. Upon cooling to room temperature, the reaction mixture was diluted with dichloromethane, passed through a celite plug and the solvents evaporated under reduced pressure. The residual oil thus obtained was purified by flash column chromatography (30% dichloromethane in hexanes) to yield 5.2 g (75%) of an off-white solid. m.p. 110-111° C. $^1$H NMR (400 MHz, CHCl$_3$) δ 2.28 (s, 3H), 3.42 (s, 3H), 6.91 (m, 7H), 7.15 (m, 4H), 7.39 (t, J=7.6 Hz, 1H), 7.66 (d, J=7.6 Hz, 1H). $^{13}$C NMR (100 MHz, CHCl$_3$) δ 20.7, 51.7, 121.6, 122.0, 123.5, 123.8, 128.5, 128.7, 128.8, 129.6, 131.1, 132.1, 132.5, 145.1, 146.7, 148.0, 167.9. HRMS (EI) calc for C$_{21}$H$_{19}$NO$_2$ [M+H]$^+$ 318.1489, found 318.1481. IR (KBr plate) 693 (m), 713 (m), 753 (m), 813 (m), 1085 (m), 1125 (m), 1244 (s), 1271 (s), 1289 (s), 1320 (s), 1448 (s), 1492 (s), 1508 (s), 1594 (s), 1722 (s), 2947 (m), 3026 (m) cm$^{-1}$.

Example 22

Synthesis of 9,9-Dimethyl-10-(p-tolyl)-9,10-dihydroacridine (DHA16) and 2,9,9-Trimethyl-10-phenyl-9,10-dihydroacridine (DHA17)

A flame-dried Schlenk flask was charged with 1.0 g methyl N-(p-tolyl)-N-phenylanthranilate (22, 3.1 mmol) and 45 mL dry, degassed Et$_2$O under argon and cooled to 0° C. in an ice bath. 2.5 Equivalents of 3.0 M methyl magnesium bromide in Et$_2$O (2.7 mL) was added dropwise and the reaction allowed to stir at room temperature under argon for 3 d. After quenching with saturated ammonium chloride, the organic layer was separated, washed with brine and water and dried over MgSO$_4$, and the solvent evaporated under reduced pressure. The crude tertiary alcohol thus formed was carried on to the next step without purification. To the neat oil isolated from the previous step was added 1-2 mL of concentrated H$_2$SO$_4$ under argon and the reaction stirred at room temperature for 1 h under argon. After dilution with 30 mL DI H$_2$O the reaction was poured into a 10% (v/v) aqueous ammoniacal solution and extracted with ether (5×50 mL). The combined organic layers were washed with saturated sodium bicarbonate, brine and water and dried over MgSO$_4$, and the solvent evaporated under reduced pressure. The residue was purified by flash column using gradient elution, starting with 10% dichloromethane in hexanes and progressing to 50% dichloromethane in hexanes. 0.52 g (55%) of a mixture of DHA16 and DHA17 as white solid was isolated. DHA16 and DHA17 could not be separated from each other. m.p. 100-102° C. $^1$H NMR (400 MHz, CHCl$_3$) δ 1.66 (s, 9H), 2.27 (s, 3H), 2.46 (s, 3H), 6.13 (d, J=8.4 Hz, 1H), 6.22 (dd, J=1.2, 8.0 Hz, 1H), 6.26 (dd, J=1.2, 8.0 Hz, 1H), 6.74 (dd, J=1.2, 8.0 Hz, 1H), 6.92 (m, 5H), 7.18 (d, J=8.4 Hz, 2 H), 7.30 (d, J=8.4 Hz, 2H), 7.43 (m, 5H), 7.59 (m, 2H). $^{13}$C NMR (100 MHz, CHCl$_3$) δ 21.0, 21.6, 31.5, 31.6, 35.0, 36.2, 114.1, 114.3, 114.3, 120.4, 120.6, 125.4, 125.5, 126.1, 126.5, 126.6, 127.2, 128.4, 129.8, 130.1, 130.1, 130.2, 131.1, 131.2, 131.6, 131.8, 138.2, 138.7, 139.0, 141.3, 141.7. HRMS (ESI) calc for C$_{22}$H$_{21}$N [M+H]$^+$ 300.1747, found 300.1756. IR (KBr plate) 745 (s), 886 (m), 1037 (m), 1318 (m), 1452 (m), 1479 (s), 1507 (m), 1580 (m), 1606 (m), 2966 (m) cm$^{-1}$.

Example 23

Synthesis of Methyl N-(2-mesityl)-N-phenylanthranilate (24)

A flame-dried Schlenk flask was charged with 14 (5 g, 22 mmol), 2-bromomesitylene (3.67 mL, 4.77 g, 24 mmol), copper powder (1.56 g, 24 mmol), copper (I) iodide (100 mg), potassium carbonate (3.3 g, 24 mmol), and 5 mL hexyl ether under argon. The resulting mixture was heated to 190° C. in a sand bath for 24 h. Upon cooling to room temperature, the reaction mixture was diluted with dichloromethane, passed through a celite plug and the solvents evaporated under reduced pressure. The residual oil thus obtained was purified by flash column chromatography (30% dichloromethane in hexanes) to yield 4.18 g (55%) of an off-white solid. m.p. 90° C. $^1$H NMR (400 MHz, CHCl$_3$) δ 2.03 (s, 6H), 2.30 (s, 3H), 3.26 (s, 3H), 6.65 (dd, J=0.8 Hz, 8.4 Hz, 1H), 6.81 (m, 3H), 6.93 (m, 3H), 7.11 (m, 2H), 7.21 (m, 1H), 7.60 (dd, J=1.6, 7.6 Hz, 1H). $^{13}$C NMR (100 MHz, CHCl$_3$) δ 19.0, 21.2, 51.5, 114.2, 117.3, 119.4, 121.1, 121.3, 122.5, 122.7, 123.2, 129.0, 129.3, 129.3, 129.6, 130.3, 130.5, 131.4, 131.9, 132.7, 134.3, 136.4, 136.9, 137.8, 138.1, 140.9, 145.0, 148.4, 168.9. HRMS (EI) calc for C$_{23}$H$_{23}$NO$_2$ [M+H]$^+$ 346.1802, found 346.1804. IR (KBr plate) 741 (m), 756 (m), 1238 (m), 1319 (m), 1448 (s), 1483 (s), 1593 (s), 1719 (s), 2857 (m), 2918 (m), 2948 (m), 3026 (m) cm$^{-1}$.

Example 24

Synthesis of 9,9-Dimethyl-10-(2-mesityl)-9,10-dihydroacridine (DHA18)

A flame-dried Schlenk flask was charged with 1.0 g methyl N-(2-mesityl)-N-phenylanthranilate (24, 2.9 mmol) and 45 mL dry, degassed Et$_2$O under argon and cooled to 0° C. in an ice bath. 2.5 Equivalents of 3.0 M methyl magnesium bromide in Et$_2$O (2.4 mL) was added dropwise and the reaction allowed to stir at room temperature under argon for 3 d. After quenching with saturated ammonium chloride, the organic layer was separated, washed with brine and water and dried over MgSO$_4$, and the solvent evaporated under reduced pressure. The crude tertiary alcohol thus formed was carried on to the next step without purification. To the neat oil isolated from the previous step was added 1-2 mL of concentrated H$_2$SO$_4$ under argon and the reaction stirred at room temperature for 1 h under argon. After dilution with 30 mL DI H$_2$O the reaction was poured into a 10% (v/v) aqueous ammoniacal solution and extracted with ether (5×50 mL). The combined organic layers were washed with saturated sodium bicarbonate, brine and water and dried over MgSO$_4$, and the solvent evaporated under reduced pressure. The residue was purified by flash column using gradient elution, starting with 10% dichloromethane in hexanes and progressing to 50% dichloromethane in hexanes. 0.57 g (60%) of a white solid was thus isolated. m.p. 85° C. NMR (400 MHz, CHCl$_3$) δ 1.69 (s, 6H), 1.96 (s, 6H), 2.37 (s, 3H), 6.07 (dd, J=1.6, 8.4 Hz, 2H), 6.90 (m, 4H), 7.06 (s, 2H), 7.44 (dd, J=1.6, 7.6 Hz, 2H). $^{13}$C NMR (100 MHz, CHCl$_3$) δ 18.0, 20.2, 21.4, 33.5, 36.1, 112.7, 119.8, 120.4, 120.7, 126.3, 127.2, 128.6, 128.6, 129.3, 129.7, 130.4, 135.2, 138.1, 138.5, 138.7. HRMS (ESI) calc for C$_{22}$H$_{21}$N [M+H]$^+$ 300.1747, found 300.1756. IR (KBr plate) 745 (s), 886 (m), 1315 (m), 1484 (s), 1507 (m), 1580 (m), 1606 (m), 2966 (m) cm$^{-1}$.

Example 25

Synthesis of 10,10'-dimethyl-9,9,9',9'-tetraphenyl-9, 9',10,10'-tetrahydro-2,2'-biacridine (D1)

A flame-dried Schlenk flask was charged with DHA8 (1.0 g, 2.8 mmol) and 10 mL dry dichloromethane under argon. Triethyloxonium hexachloroantimonate (1.26 g, 2.8 mmol) was added to this solution in one portion under argon. The reaction was stirred at room temperature for 12 h. A 10% aqueous solution of sodium thiosulfate was then added, the organic layer separated, washed with brine and water and dried over MgSO$_4$, and the solvent evaporated under reduced pressure. The residue was purified by flash column using 50% dichloromethane in hexanes as eluent. 0.40 g (40%) of a faint-yellow solid was thus isolated. m.p. 340° C. (decomp.). $^1$H NMR (400 MHz, CHCl$_3$) δ 3.27 (s, 6H), 6.88 (m, 18H), 7.17 (m, 16H). $^{13}$C NMR (100 MHz, CHCl$_3$) δ 33.6, 57.4, 112.0, 112.4, 120.0, 125.3, 125.9, 126.3, 126.5, 127.4, 127.5, 127.7, 127.9, 128.3, 128.7, 130.2, 130.3, 130.5, 131.3, 131.8, 132.7, 141.5, 142.7, 146.0. HRMS (ESI) calc for C$_{52}$H$_{41}$N$_2$ [M+H]$^+$ 693.3264, found 693.3267. IR (KBr plate) 638 (m), 697 (m), 733 (m), 755 (m), 1270 (m), 1357 (m), 1463 (s), 1590 (m), 1589 (m), 2815 (w), 2873 (w), 3056 (m) cm$^{-1}$.

Example 26

Synthesis of 9,9-Dimethyl-2-nitro-9,10-dihydroacridine (26)

A mixture of 0.5 g DHA1 (2.3 mmol) and 0.8 g of either RDX or PETN were dissolved in 3.0 mL dry, degassed acetonitrile and the solution photolyzed with a solar simulator (1.3 suns AM 1.5) for 60 minutes. The reaction mixture was sampled every 10 minutes to determine the GC yield of the nitrated product. Approximately 80% of 26 (GC yield) was formed after 60 minutes of photolysis. Compound 26 was isolated by flash column chromatography using 50/50 hexanes/dichloromethane as an eluent. $^1$H NMR (400 MHz, CHCl$_3$) δ 1.62 (s, 6H), 6.64 (s, 1H), 6.69 (d, J=8.8 Hz, 1H), 6.75 (d, J=8.8 Hz, 1H), 7.03 (m, 1H), 7.15 (m, 1H), 7.40 (d, J=7.6 Hz, 1H), 8.02 (dd, J=2.4, 8.8 Hz, 1H), 8.30 (s, 1H). $^{13}$C NMR (100 MHz, CHCl$_3$) δ 30.7, 36.4, 113.6, 121.8, 126.7, 127.9, 130.2, 148.6. HRMS (ESI) calc for C$_{15}$H$_{14}$N$_2$O$_2$ [M+H]$^+$ 255.1128, found 255.1123. IR (KBr plate) 753 (s), 1053 (m), 1232 (m), 1347 (m), 1383 (w), 1456 (s), 1483 (s), 1582 (s), 1615 (w), 2924 (m) cm$^{-1}$.

Example 27

Synthesis of 2-Nitro-9,9-diphenyl-9,10-dihydroacridine (28)

Method A. A mixture of 0.5 g DHA4 (1.5 mmol) and 0.8 g of either RDX or PETN were dissolved in 3.0 mL dry, degassed acetonitrile and the solution photolyzed with a solar simulator (1.3 suns AM 1.5) for 60 minutes. The reaction mixture was sampled every 10 minutes to determine the GC yield of the nitrated product. Approximately 80% of 28 (GC yield) was formed after 60 minutes of photolysis. Compound 28 was isolated by flash column chromatography using 50/50 hexanes/dichloromethane as an eluent. $^1$NMR (400 MHz, CHCl$_3$) δ 7.12 (broad m, 16H), 8.02 (dd, J=8.8, 2.2 Hz, 1H), 8.30 (d, J=2.2 Hz, 1H). $^{13}$C NMR (100 MHz, CHCl$_3$) δ 56.7, 113.5, 120.2, 125.6, 126.1, 126.2, 127.1, 127.4, 127.5, 127.6, 127.9, 128.5, 131.0, 133.2, 137.3, 142.7, 146.0, 149.3. HRMS (ESI) calc for C$_{25}$H$_{19}$N$_2$O$_2$ [M+H]$^+$ 379.1441, found 379.1447. IR (KBr plate) 699 (m), 762 (m), 907 (m), 1300 (m), 1330 (m), 1483 (s), 1529 (m), 1585 (s), 2922 (m), 3410 (m) cm$^{-1}$.

Example 28

Synthesis of 2-Nitro-9,9-diphenyl-9,10-dihydroacridine (28)

Method B. Compound 28 was also synthesized by nitrating DHA4: A 25 mL round bottom flask was charged with 0.5 g DHA4 (1.5 mmol) and 20 mL dry dichloromethane under argon and the solution was cooled to −78° C. in an acetone/dry ice bath. Approximately 0.2 g of 25% HNO$_3$ on silica gel was then added to the solution and the reaction stirred at −78° C. for 1 h. Upon warming to room temperature, the reaction was filtered and the solvent evaporated under reduced pressure. The residue was purified by flash column chromatography using 50/50 hexanes/dichloromethane as eluent. 40% of the mononitrated product (28) and 30% of the dinitrated product was thus isolated.

Example 29

Synthesis of 9,9-Dimethyl-2-nitro-10-(2-mesityl)-9, 10-dihydroacridine (30)

A mixture of 0.5 g DHA18 (1.5 mmol) and 0.8 g of either RDX or PETN were dissolved in 3.0 mL dry, degassed acetonitrile and the solution photolyzed with a solar simulator (1.3 suns AM 1.5) for 60 minutes. The reaction mixture was sampled every 10 minutes to determine the GC yield of the nitrated product. Approximately 82% of 30 (GC yield) was formed after 60 minutes of photolysis. Compound 30 was isolated by flash column chromatography using 50/50 hexanes/dichloromethane as an eluent. $^1$H NMR (400 MHz, CHCl$_3$) δ 1.74 (s, 6H), 1.96 (s, 6H), 2.41 (s, 3H), 6.11 (d, J=9.2 Hz, 1H), 6.17 (dd, J=2.8, 8.0 Hz, 1H), 7.01 (m, 2H), 7.11 (s, 2H), 7.48 (m, 1H), 7.84 (dd, J=2.4, 9.2 Hz, 1H), 8.36 (d, J=2.8 Hz, 1H). $^{13}$C NMR (100 MHz, CHCl$_3$) δ 17.8, 21.4, 33.6, 36.3, 68.8, 112.4, 113.8, 122.8,123.2, 123.9, 126.4, 127.7, 129.7, 130.0, 130.7, 134.1, 137.0, 137.5, 139.1, 141.0, 144.1. HRMS (ESI) calc for C$_{24}$H$_{25}$N$_2$O$_2$ [M+H]$^+$ 373.1911, found 373.1913. IR (KBr plate) 750 (m) 848 (m), 1289 (s), 1306 (s), 1320 (s), 1475 (s), 1496 (s), 1592 (m), 1651 (s), 2918 (m), 2969 (m) cm$^{-1}$.

Example 30

Synthesis of 9,9-Diethyl-2-nitro-9,10-dihydroacridine (31) and 9-Ethyl-9-vinyl-9,10-dihydroacridine (33)

A mixture of 0.5 g DHA2 (2.1 mmol) and 0.8 g of either RDX or PETN were dissolved in 3.0 mL dry, degassed acetonitrile and the solution photolyzed with a solar simulator (1.3 suns AM 1.5) for 60 minutes. Compounds 31 and 33 were isolated by flash column chromatography using 50/50 hexanes/dichloromethane as an eluent. Compound 33 co-eluted with unreacted DHA2 and, therefore, could not be completely separated from DHA2. Compound 31: $^1$H NMR (400 MHz, CHCl$_3$) δ 0.59 (t, J=7.2 Hz, 6H), 1.96 (quartet, J=7.2 Hz, 4H), 6.47 (s, 1H), 6.60 (d, J=8.8 Hz, 1H), 6.67 (d, J=1.2 Hz, 1H), 7.00 (m, 1H), 7.12 (m, 1H), 7.24 (m, 1H), 7.97 (d, J=2.8 Hz, 1H), 8.00 (s, 1H). $^{13}$C NMR (100 MHz, CHCl$_3$) δ 9.7, 38.8, 46.3, 112.9, 114.1, 122.8, 123.9, 124.1, 124.5, 125.2, 127.0, 127.4, 137.6, 145.2. HRMS (ESI) calc for C$_{17}$H$_{19}$N$_2$O$_2$ [M+H]$^+$ 283.1441, found 283.1443. IR (KBr plate) 746 (m), 823 (m), 1242 (s), 1282 (s), 1294 (s), 1329 (m), 1462 (m), 1487 (s), 1530 (s), 1578 9s), 1609 (m), 2932 (m), 2968 (m), 3352 (s) cm$^{-1}$. Compound 33: $^1$H NMR (400 MHz, CHCl$_3$) δ 0.91 (t, J=7.6 Hz, 3H), 0.97 (t, J=7.6 Hz, 3H), 1.48 (d, J=6.8 Hz, 2H), 1.79 (d, J=6.8 Hz, 3H), 2.24 (q, J=7.6 Hz, 2H), 2.35 (q, J=7.6 Hz, 2H), 5.48 (m, 1H), 5.72 (m, 1H), 5.74 (s, 1H), 6.90 (m, 4H), 7.06 (m, 5H). $^{13}$C NMR (100 MHz, CHCl$_3$) δ 13.0, 13.1, 13.9, 14.8, 24.3, 31.7, 115.9, 116.8, 118.2, 118.5, 120.3, 120.5, 121.0, 121.2, 123.0, 124.9, 127.4, 127.5, 129.5, 129.7, 130.1, 130.2, 134.3, 140.1, 140.3, 141.2, 143.5, 143.7. HRMS (ESI) calc for C$_{17}$H$_{17}$N [M+H]$^+$ 236.1434, found 236.1438. IR (KBr plate) 692 (m), 745(m), 1309(m), 1451 (m), 1506(s), 1575 (m), 1594 (s), 2925(m), 2963(m), 3405 (m) cm$^{-1}$.

Example 31

The following example describes the design of an indicator for use in the determination of analytes such as RDX and PETN.

Considering the electrophilic nature of the NO$_x$ species generated by the photofragmentation of RDX and PETN and their resemblance to the active electrophiles in aromatic nitration reactions, reactions between electron-rich tertiary aromatic amines and the photofragments of RDX and PETN were selected. It was found that photolysis (λ=313 nm) of a mixture of N,N-dimethylaniline (DMA) and 2 equivalents of either RDX or PETN for 10 minutes in acetonitrile under anaerobic conditions afforded the formation of N,N-dimethyl-4-nitroaniline (DMNA) in 14% yield (GC yield). Higher yields of DMNA were obtained with longer photolysis times and DMNA was formed in ca. 80% yield after 1 hour. The photoreaction between DMA and either RDX or PETN under anaerobic conditions was observed to produce only a single, yellow-colored product (DMNA) and other side products were not evident by TLC or GC-MS analyses. The $^1$H-NMR, IR and high-resolution mass spectra of the isolated yellow product matched those obtained for an authentic commercial sample of DMNA. Conducting the photolysis under aerobic conditions resulted in partial demethylation of DMA and yielded a mixture of DMNA and its demethylated analog, N-methyl-4-nitroaniline (13) (see Scheme 1). Photolysis of DMA with ammonium nitrate was also found to produce DMNA, although relatively longer photolysis times (>30 minutes) were required and greater amounts of demethylated side products were observed (possibly due to the presence of water or other nucleophiles in the solutions).

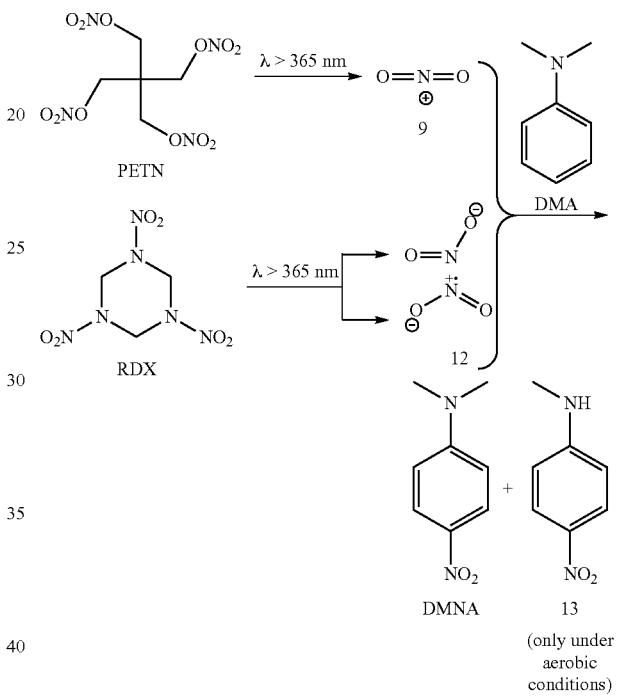

Scheme 1. Nitration of N,N-dimethylaniline with the photofragmentation products of RDX and PETN.

A distinct absorbance band centered at 400 nm was found to accompany the formation of the nitrated products under both aerobic and anaerobic conditions, which also matched the low-energy charge-transfer band displayed by commercial DMNA. However, DMNA has a very low fluorescence quantum yield and, therefore, a significant turn-on fluorescence signal was not generated upon reaction of DMA with the photofragmentation products of RDX and PETN.

To probe the scope of the photonitration reaction, the nitration of 9,9-dioctylfluorene, anisole and 1,2-dimethoxybenzene by RDX and PETN was investigated. Extended photolysis (5 h) of a mixture of 9,9-dioctylfluorene and either RDX or PETN in 1:1 acetonitrile:THF at either 254, 313, 334, or 356 nm did not generate any observable products and 9,9-dioctylfluorene was recovered in ca. 90% yield. Photolysis of anisole with RDX or PETN yielded only trace amounts of 4-nitroanisole (<1% GC yield) after 4 hours. Photolysis of 1,2-dimethoxybenzene with either RDX or PETN yielded 1,2-dimethoxy-4-nitrobenzene in only ca. 8% yield after 2 hours; moreover this reaction did not proceed cleanly and numerous polar photoproducts were observed. Based on this set of experiments, anilines were selected as candidates for potential indicators. To create fluorogenic indicators based on the facile nitration reaction between aromatic amines and the photofragmentation products of RDX and PETN, 9,9-disubstituted 9,10-dihydroacridines (DHAs) were targeted as chemosensory.

Example 32

Figure 4A:
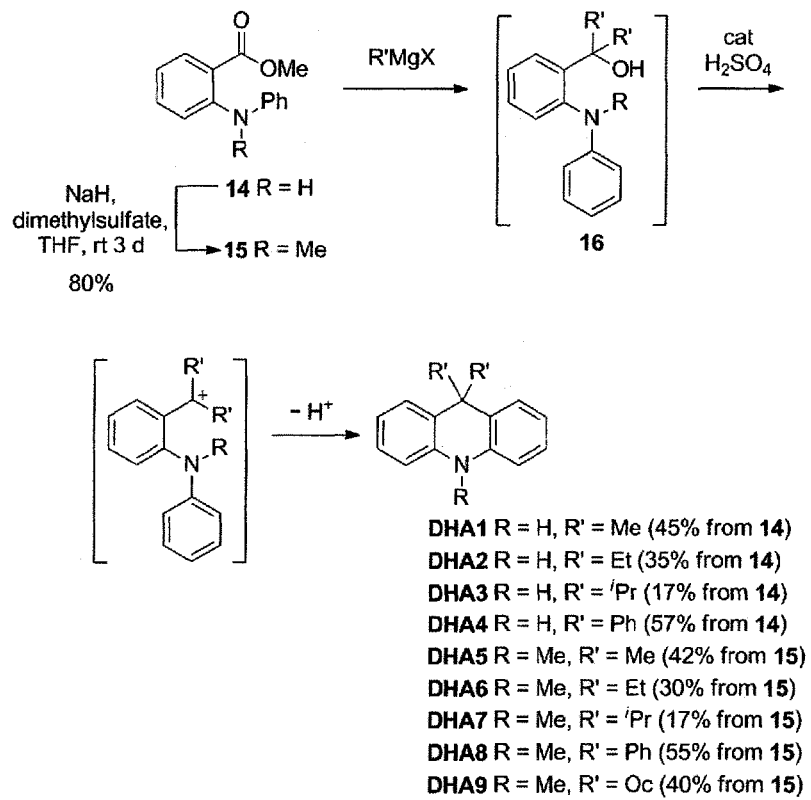
FIG. 4 shows (a) the synthesis of 9,9-disubstituted 9,10-dihydroacridines via Route A; (b) the synthesis of 9,9-disubstituted DHAs via Route B; and (c) the synthesis of N-aryl DHAs via Route C.
Figure 4B:
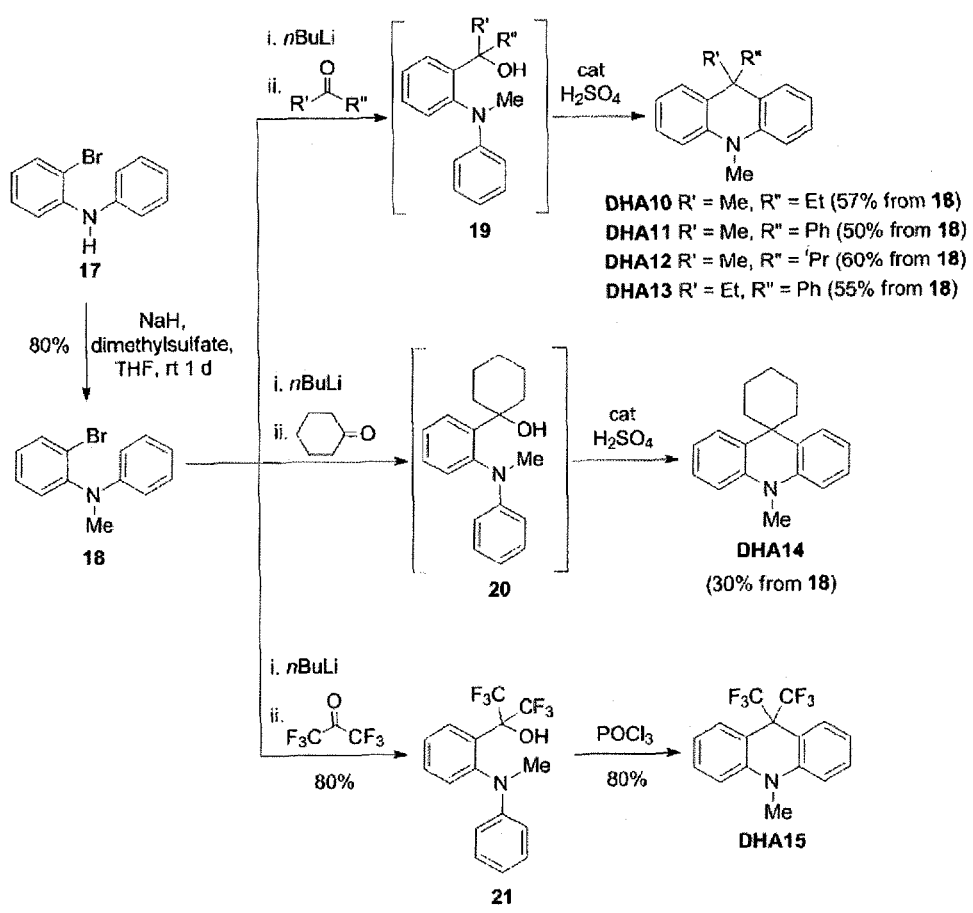
Figure 4C:
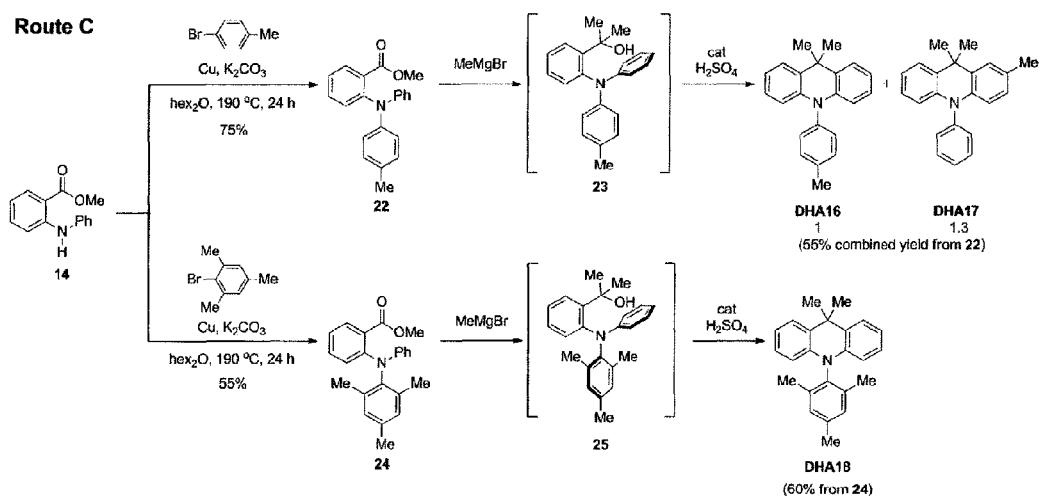
Figure 5:
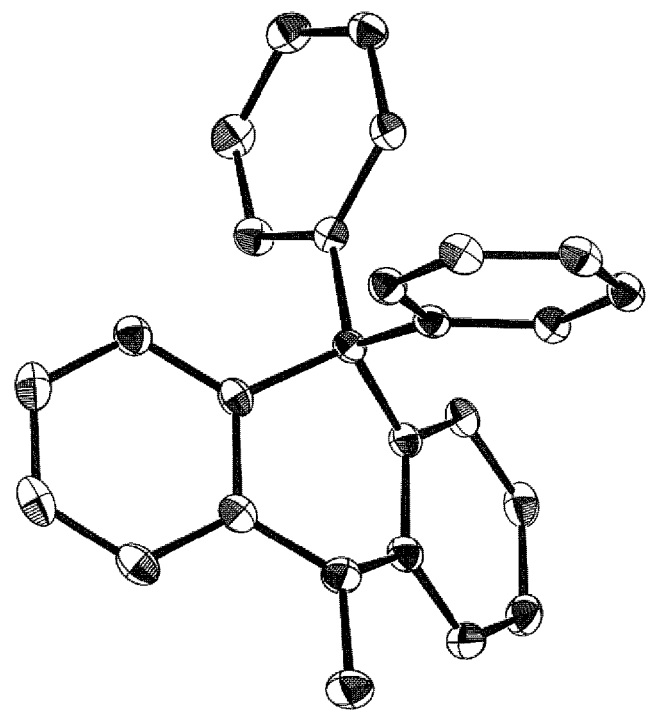
FIG. 5 shows an X-ray crystal structure of DHA8.

The following example describes the synthesis of various DHA indicators. As shown in Schemes 3-5, a series of 9,9-disubstituted DHAs were synthesized, starting from either N-phenylanthranilic acid methyl ester (FIG. 4C and FIG. 4C) or a diphenylamine derivative (FIG. 4B). DHAs were accessed by an acid-catalyzed cyclization of a tertiary alcohol intermediate (for example, structure 16). In FIG. 4A (Route A), intermediate 16 is accessed by a double 1,2-addition of an alkyl or aryl Grignard reagent to either N-phenylanthranilic acid methyl ester (14) or its N-methyl derivative (15). In FIG. 4B (Route B), tertiary alcohol intermediates 19-21 are accessed from 1,2-addition of the aryl lithium species derived from 18 to an appropriate ketone. This strategy was adopted to synthesize asymmetric DHAs (DHA10-13) that have two different substituents at the 9-position, a Spiro-DHA (DHA14), and a $CF_3$-containing DHA (DHA15). In most cases described in this Example, adding a catalytic amount of concentrated sulfuric acid resulted in Friedel-Crafts reaction/cyclization of the respective tertiary alcohol intermediates to yield 9,9-disubstituted DHAs. Without wishing to be bound by theory, this transformation may proceed via formation of a carbocation. The X-ray crystal structure of DHA8 thus obtained is shown in FIG. 5. While the use of strong acids, Lewis acids, or thionyl chloride under these conditions were not shown to yield DHA15, it was found that refluxing a solution of 21 in $POCl_3$ produced DHA15 in high yield.

Lastly, Route C (FIG. 4C) was followed to synthesize N-aryl DHAs. Copper-catalyzed N-arylation of 14 with 4-bromotoulene initially furnished 22, which was then reacted with 2.5 equivalents of methylmagnesium bromide and catalytic concentrated sulfuric acid. The Friedel-Crafts cyclization of intermediate 23 yielded a nearly-statistical mixture of DHA16 and DHA17 (1:1.3 DHA16:DHA17), which could not be sufficiently separated by either column chromatography or recrystallization. Therefore, compound 24 was synthesized by copper-catalyzed N-arylation of 14 with 2-bromomesitylene and subsequently reacted with methylmagnesium bromide and sulfuric acid to access DHA18.

Example 33

The following example describes the study of the photophysical properties of DHA1-18. The optical properties of DHA1-18 are summarized in Table 1 shown below. The DHAs reported herein displayed similar UV-vis absorption spectra, with absorption maxima around 290 nm. Additionally, DHA1-18 generally displayed a single emission band centered at ca. 350 nm and were found to have similar fluorescence quantum yields and excited-state lifetimes.

TABLE 1

Optical Properties of DHAs in acetonitrile.

| Cmpd | $\lambda_{max}$/nm (log ε) | $\lambda_{em}$/nm | $\Phi^a$ | τ/ns |
|---|---|---|---|---|
| DHA1 | 284 (4.1) | 352 | 0.18 | 2.7 |
| DHA2 | 288 (4.1) | 390 | 0.04 | 2.2 |
| DHA3 | 288 (4.1) | 376 | 0.09 | 2.7 |
| DHA4 | 285 (4.0), 320 (3.8) | 355 | 0.13 | 1.6 |
| DHA5 | 285 (4.1) | 355 | 0.14 | 2.8 |
| DHA6 | 246 (4.1), 290 (4.0) | 382 | 0.12 | 2.3 |
| DHA7 | 257 (4.1), 298 (3.9) | 345 | 0.10 | 2.7 |
| DHA8 | 294 (3.9) | 359 | 0.14 | 1.7 |
| DHA9[b] | 247 (4.1), 290 (3.9) | 345 | 0.15 | 2.8 |
| DHA10 | 246 (4.3), 290 (4.1) | 352 | 0.12 | 2.5 |
| DHA11 | 289 (4.3) | 355 | 0.14 | 1.7 |
| DHA12 | 247 (4.0), 292 (3.9) | 382 | 0.06 | 1.7 |
| DHA13 | 245 (4.8), 296 (4.4) | 355 | 0.09 | 2.2 |
| DHA14 | 247 (4.0), 297 (3.8) | 345 | 0.15 | 2.4 |
| DHA15 | 280 (4.3), 311 (4.0) | 354 | 0.18 | 2.5 |
| DHA16 + DHA17 | 290 (4.2) | 371 | 0.05 | 2.7 |
| DHA18 | 290 (4.2) | 371 | 0.03 | 2.5 |

[a]Measured against quinine sulfate in 0.1N $H_2SO_4$ (Φ 0.54)
[b]in THF

Example 34

The following example describes the study of the electrochemical properties of some DHAs described herein.

Figure 6:
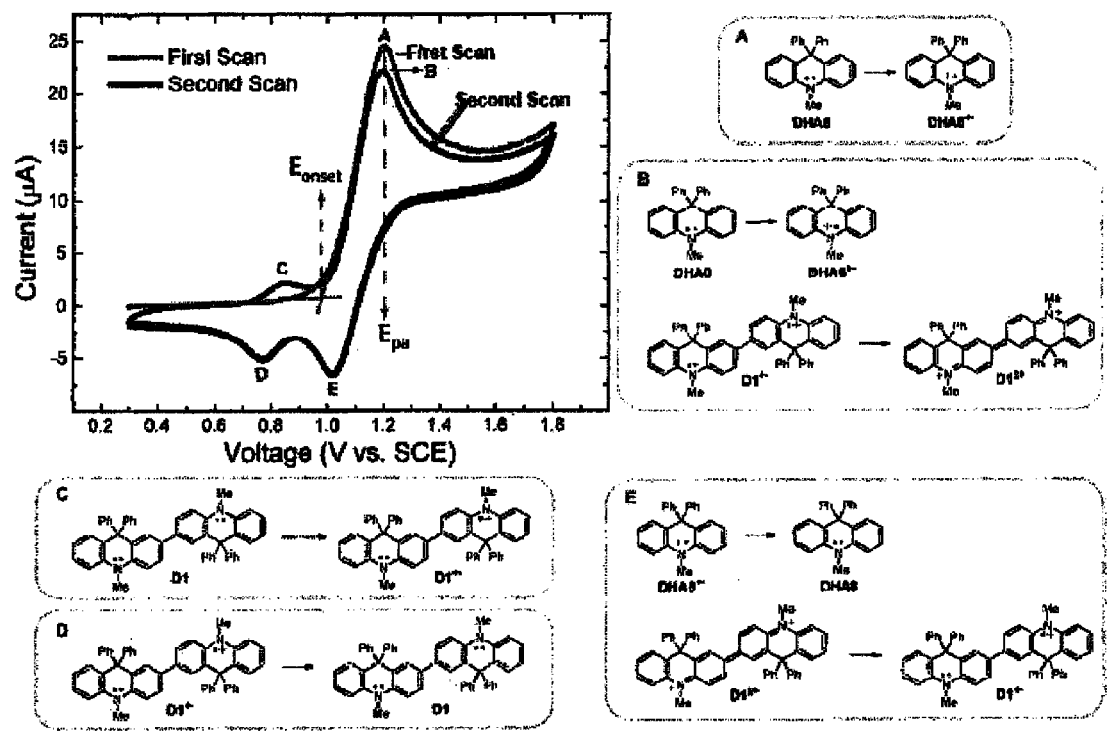
FIG. 6 shows the cyclic voltammogram of DHA8 (Pt button electrode, 0.1 M $TBAPF_6$ in $CH_2Cl_2$, 100 mV/s).

Cyclic voltammograms (CVs) of select DHAs were recorded in $CH_2Cl_2$ with tetrabutylammonium hexafluorophosphate ($TBAPF_6$) as a supporting electrolyte and were found to reveal behavior suggestive of irreversible chemical transformations. As a representative example, FIG. 6 shows the cyclic voltammogram of DHA8 (Pt button electrode, 0.1 M $TBAPF_6$ in $CH_2Cl_2$, 100 mV/s). The redox reactions giving rise to each anodic (A, B and C) and cathodic (D and E) peak are shown, and the first anodic peak potential ($E_{pa}$) and onset potential ($E_{onset}$) for the first scan are labeled. The first anodic sweep resulted in a single oxidation peak at ca. 1.20 V vs. SCE, which can be ascribed to the formation of the radical cation of DHA8. However, the corresponding cathodic sweep revealed two cathodic peaks, arising from the reduction of two different species in solution. Furthermore, a subsequent anodic sweep displayed two oxidation peaks. Such behavior has been previously observed for triphenylamine (TPA), and can be attributed to the rapid dimerization of TPA radical cations following oxidation; the electroactive TPA dimer thus formed leads to the growth of an additional anodic and cathodic peak after an initial anodic sweep. Based upon assignments made for the CV of TPA, the redox reactions responsible for the individual anodic and cathodic peaks observed in the CV of DHA8 were identified and are shown in FIG. 6.

Figure 7:
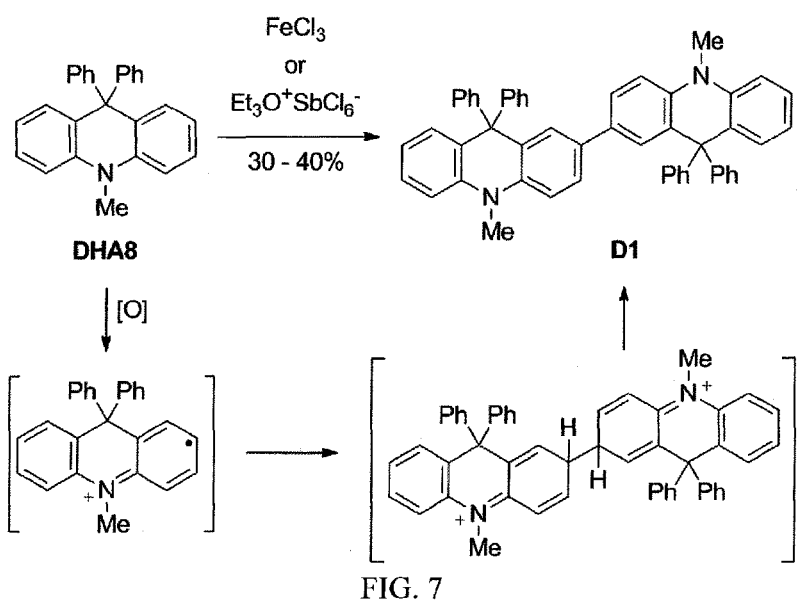
FIG. 7 shows the proposed oxidative dimerization of a dihydroacridine compound.

The dimerization of radical cations of DHA8 in the electrochemical cell to form D1 was confirmed by independently synthesizing D1. FIG. 7 shows the oxidative dimerization of DHA8 with $FeCl_3$ or [$Et_3O^+SbCl_6$] to form D1 in 30-40% yield. This oxidation reaction was found to selectively yield the dimeric product (by TLC and crude $^1$H NMR analyses); moreover, the remaining, unreacted DHA8 was recovered upon reaction workup. The use of hydrogen peroxide and tert-butyl-hydrogen peroxide was also investigated; however, D1 was only formed in less than 5% yield with these reagents and DHA8 was recovered in ca. 90% yield after reaction workup. Attempts to affect an oxidative polymerization of DHA8 were not successful and only D1 was isolated. Without wishing to be bound by theory, his observation can be explained by the fact that D1, once formed, can be oxidized to a stable, closed-shell dication ($D1^{2+}$, see FIG. 6) that generally does not participate in subsequent radical coupling reactions to form polymers. Dimer D1 is a faint-yellow compound that displays an absorption band centered at 457 nm and an emission band centered at 478 nm ($\Phi$0.20). The CV of D1 was found to match the second scan of the CV of DHA8 (FIG. 6), confirming the aforementioned assignments for the anodic and cathodic peaks observed in the CV of DHA8.

The electrochemical behavior of DHA8 was similar to that of the rest of the reported DHAs and also similar to the electrochemical behavior of DMA—i.e., the respective radical cations dimerized in the electrochemical cell after the first anodic sweep. The values for the first anodic peak potential ($E_{pa}$) and onset potential ($E_{onset}$) for the first scan of the CVs of select DHAs, DMA and TPA are summarized in Table 2 shown below. In general, similar values of $E_{pa}$ and $E_{onset}$ were observed for most DHAs; however, the electron-deficient, $CF_3$-containing DHA15 displayed significantly higher $E_{pa}$ and $E_{onset}$ values.

TABLE 2

Electrochemical Properties of Select DHAs.

| Cmpd | $E_{pa}$/V vs SCE | $E_{onset}$/V vs SCE |
| --- | --- | --- |
| DHA1 | 1.19 | 0.77 |
| DHA2 | 1.05 | 0.77 |
| DHA4 | 1.07 | 0.87 |
| DHA5 | 1.27 | 0.86 |
| DHA6 | 1.30 | 0.86 |
| DHA7 | 1.51 | 0.92 |
| DHA8 | 1.20 | 0.95 |
| DHA9 | 1.35 | 0.85 |
| DHA11 | 1.08 | 0.87 |
| DHA15 | 1.65 | 1.18 |
| DHA16 + DHA17 | 1.04 | 0.83 |
| DHA18 | 1.08 | 0.83 |
| DMA[a] | 1.36 | 0.77 |
| TPA[b] | 1.48 | 0.95 |

[a]N,N-Dimethylaniline.
[b]Triphenylamine.

Example 34

In the following example, the reaction of various DHA compounds with RDX/PETN photofragmentation products was studied.

The photoreactions between DHA1-18 and either RDX or PETN were initially investigated in acetonitrile solutions. In general, irradiating solutions containing DHA1-18 and either RDX or PETN (which were initially colorless) at 313 nm under aerobic conditions led to the evolution of a bright yellow/orange color after approximately 30 seconds to 5 minutes. Irradiating solutions of DHA1-18 in the absence of either RDX or PETN did not result in the same bright yellow/orange color, although faint yellowing of the DHA solutions was noticed after greatly extended exposure (>60 minutes) to UV light under aerobic conditions.

The photolyses ($\lambda$=313 nm) of select DHAs with a stoichiometric amount of either RDX or PETN were conducted on a preparative scale in order to isolate and characterize the reaction products formed. In these studies, long irradiation times (generally 60 minutes) were employed to ensure complete reactant conversion. TLC and GC-MS analyses of crude reaction mixtures indicated that only a single, highly-colored product was formed in all cases. The yellow-orange products from the reactions of DHA1, DHA4, and DHA18 with either RDX or PETN were isolated by flash column chromatography and identified to be the mono-nitrated structures (26, 28, and 30, respectively) shown in FIG. 8 by their $^1$H NMR, FT-IR and high resolution mass spectra. Compounds 26, 28 and 30 were isolated in 70-80% yield after column chromatography, along with ca. 10-15% of unreacted DHA1, DHA4, or DHA18. Similarly, DHA5 and DHA8 were confirmed to produce 27 and 29, respectively, in approximately 70% yield (GC yield) upon photolysis with RDX or PETN (30 minutes). Additionally, DHA1 and DHA4 were independently nitrated under mild conditions using $SiO_2$:$HNO_3$ and the products thus obtained were found to match those isolated from the photoreactions of DHA1 and DHA4 with RDX/PETN.

The photoreaction of DHA2 with either RDX or PETN yielded the nitrated product 31; however, compound 33 was also isolated from the reaction mixture. The yield of 33 was found to be somewhat dependent on the concentration of DHA2, with a higher amount of 33 over 31 observed in dilute solutions. The yield of 33 was also higher relative to that of 31 when the photolysis of DHA2 and RDX/PETN was conducted in slightly wet acetonitrile. Compounds 31 and 33 were generally isolated in 80% combined yield after flash column chromatography of the photoreactions between DHA2 and either RDX or PETN. Furthermore, DHA6 was confirmed to produce 32 and 34 (by GC-MS analysis) upon photolysis in the presence of RDX/PETN. Without wishing to be bound by theory, compounds 33 and 34 may have been formed as a result of either H. or hydride abstraction reactions between DHA2 or DHA6 and the photodegradation products of RDX and PETN. GC-MS analyses of the photoreactions between the remaining DHAs (DHA3, DHA7, DHA9, DHA10-17) and either RDX or PETN similarly revealed the formation of mono-nitrated derivatives of the respective DHAs.

Additionally, the photoreactions between DHA1-18 and a model nitramine or nitroester compound—N,N-diisopropylnitramine (NA) and amyl nitrate (AN), respectively, as shown below—were also investigated.

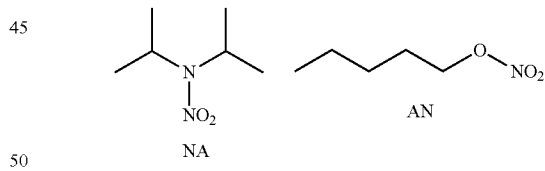

The reaction products observed upon photolysis ($\lambda$=313 nm) of mixtures of DHA1-18 and either NA or AN were essentially identical (as established by TLC and GC-MS analyses) to the aforementioned nitrated products observed with RDX and PETN. However, the observed yields (GC yields) of nitrated DHAs were significantly lower with NA/AN, as compared to RDX/PETN. For example, whereas 26 was formed in 75% yield upon photolysis with either RDX or PETN for 30 minutes, the photolysis of DHA1 with NA or AN afforded 26 in only 30% yield under identical reaction conditions. Based on these observations, RDX and PETN were more susceptible to photolytic cleavage than their respective model compounds under these conditions.

Figure 8:
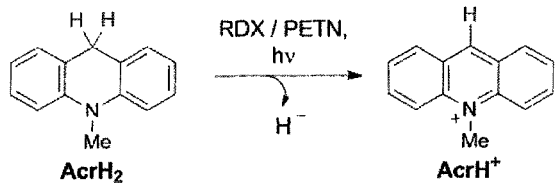
FIG. 8 illustrates photoreactions of various 9,10-dihydroacridines with RDX and PETN.
Figure 8:
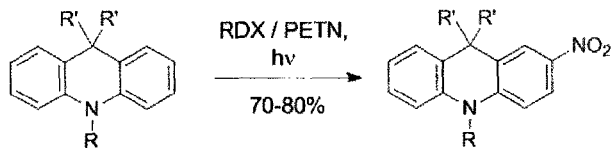
Figure 8:
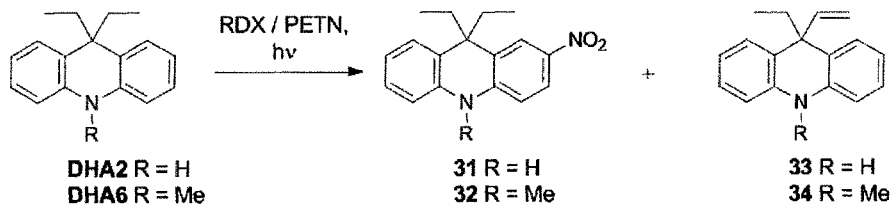

As shown in FIG. 8, it is interesting to note the difference in photochemical reaction mechanisms between various 9,10-dihydroacridines. Previous studies reported that N-methyl-9,10-dihydroacridine (AcrH$_2$) can participate in a hydride transfer reaction with either RDX, PETN, NA or AN. However, dialkylation or diarylation of the 9-position of AcrH$_2$ has been shown to facilitate the photonitration reaction described herein.

Precise timing and sophisticated, high-intensity light sources were not found to be necessary to effect the reaction between DHA1-18 and the degradation products of either RDX or PETN. Simply exposing a mixture of DHA1-18 and RDX/PETN to polychromatic light from a solar simulator effected the photolytic cleavage of RDX/PETN and subsequent formation of mono-nitrated DHAs. For example, compounds 26 and 28 could both be isolated in 75% yield (after flash column chromatography) after a mixture of RDX or PETN and DHA1 or DHA4, respectively, in acetonitrile were exposed to simulated sunlight for 45 minutes. The yields of. compounds 26 and 28 thus obtained are similar to those reported earlier for photolysis at 313 nm.

The (photo)reactions of DHA1-18 with sodium nitrite, potassium nitrate, and NO were also investigated to study the limitations of using DHA1-18 as stand-off indicators for RDX/PETN. Exposing a mixture of either DHA1, DHA5, DHA4 or DHA8 and excess sodium nitrite in 2:1 acetonitrile:water to simulated sunlight for 2 hours did not result in significant nitration of these DHAs (<1% GC yields of 26-29 were generally observed). However, upon addition of 100 μL acetic acid to the same reaction mixtures, compounds 26-29 were formed in approximately 8% yield in the absence of light. Protonating nitrite salts generates nitrous acid, which is known to decompose and form HNO$_3$ (among other species), which, without wishing to be bound by theory, may have nitrated the DHAs in this case. The addition of a large excess of monomeric NO gas to dry, oxygen-free solutions of the aforementioned DHAs failed to generate the characteristic yellow-orange color of 26-29; however, upon introduction of oxygen to these solutions, the nitrated DHAs were observed to be formed by eye (in the absence of light). Subsequent GC-MS analyses confirmed that 26-29 were formed in ca. 20% yield. Once again, NO is known to form nitrogen dioxide upon exposure to oxygen, which, without wishing to be bound by theory, may have resulted in nitration of the DHAs.

Mixtures of DHA1, DHA5, DHA4 or DHA8 and a large excess of potassium nitrate in 2:1 acetonitrile:water did not immediately result in nitration. If left standing for 24 h, 26-29, along with multiply-nitrated derivatives of the aforementioned DHAs, were formed in less than 5% combined yield (GC yield). Adding acetic acid to DHA/KNO$_3$ mixtures resulted in the formation of multiply nitrated DHAs, with 2,7-dinitro DHAs being the major products. Exposing mixtures of either DHA1, DHA5, DHA4 or DHA8 and a large excess of potassium nitrate in 2:1 acetonitrile:water to simulated sunlight for 60 minutes similarly yielded multiply-nitrated derivatives of these DHAs in approximately 20% combined yield. In this set of experiments, stoichiometric or substoichiometric amounts of potassium nitrate or shorter irradiation times did not generate observable quantities of nitrated DHAs.

Example 35

Optical properties of the nitrated DHAs described above were studied. The photophysical properties of select nitrated DHAs, which were either isolated from the photolysis reactions between DHAs and RDX/PETN or synthesized by nitrating an appropriate DHA, are listed in Table 3. In general, the nitrated DHAs displayed similar absorbance bands as DMNA, with the lowest energy bands centered at ca. 400 nm. Additionally, emission bands centered at ca. 540 nm were observed for all isolated mono-nitrated DHAs. The fluorescence quantum yields of the compounds listed in Table 3 were found to be solvent dependent, with the lowest quantum yields observed in acetonitrile. Moreover, compounds 26, 28, 30 and 31 were found to display significant emission in the solid state (in cellulose acetate films containing 10 wt % of the appropriate compound).

TABLE 3

Optical properties of select mono-nitrated DHAs.

| Cmpd | $\lambda_{max}^a$ (log ε) | $\lambda_{em}^a$ | Φ |
| --- | --- | --- | --- |
| DMNA | 395 (3.9) | 530 | <0.01 (MeCN)$^b$ |
|  |  |  | 0.09 (CHCl$_3$)$^b$ |
|  |  |  | 0.17 (film)$^{c,d}$ |
| 26 | 408 (4.1) | 535 | 0.09 (MeCN)$^b$ |
|  |  |  | 0.27 (CHCl$_3$)$^b$ |
|  |  |  | 0.35 (film)$^{c,d}$ |
| 28 | 410 (4.1) | 540 | 0.10 (MeCN)$^b$ |
|  |  |  | 0.30 (CHCl$_3$)$^b$ |
|  |  |  | 0.42 (film)$^{c,d}$ |
| 30 | 413 (4.2) | 548 | 0.14 (MeCN)$^b$ |
|  |  |  | 0.37 (CHCl$_3$)$^b$ |
|  |  |  | 0.45 (film)$^{c,d}$ |
| 31 | 409 (4.1) | 539 | 0.05 (MeCN)$^b$ |
|  |  |  | 0.22 (CHCl$_3$)$^b$ |
|  |  |  | 0.33 (film)$^{c,d}$ |

$^a$in MeCN
$^b$Measured against perylene in EtOH (Φ 0.94)
$^c$10 wt % in cellulose acetate
$^d$Measured against 10 wt % perylene in PMMA (Φ 0.78)

Example 36

Figure 9:
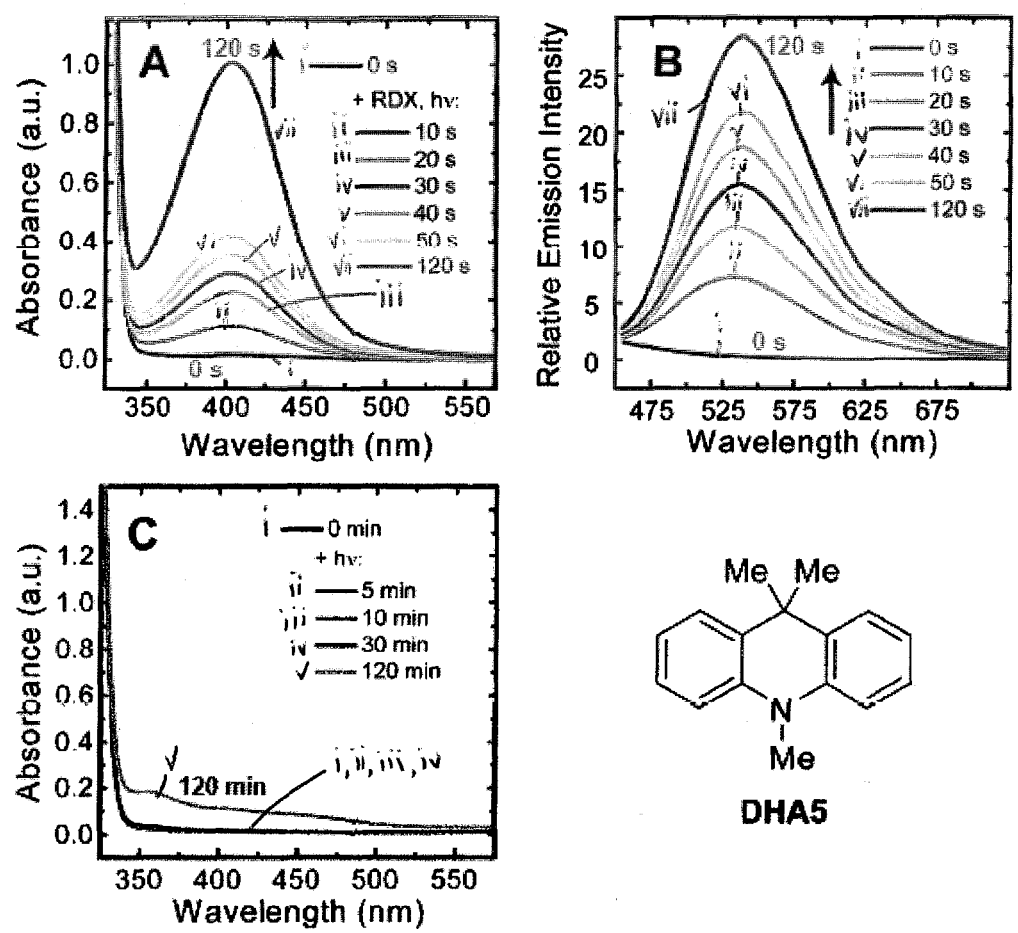
FIG. 9 shows the (a) absorption profile and (b) emission profile (B, $\lambda_{ex}$=415 nm) for the photoreaction reaction between DHA5 and RDX under aerobic conditions in acetonitrile upon irradiation at 313 nm ([DHA5]=$1.3\times10^{-4}$ M. [RDX]=$5.4\times10^{-5}$ M), as well as (c) the absorption profile for the extended irradiation of a blank, aerated solution of DHA5.

In the following example, the optical properties of the indicators were investigated. FIG. 9 shows the (a) absorption profile and (b) emission profile (B, $\lambda_{ex}$=415 nm) for the photoreaction reaction between DHA5 and RDX under aerobic conditions in acetonitrile upon irradiation at 313 nm ([DHA5]=1.3×10$^{-4}$ M, [RDX]=5.4×10$^{-5}$ M), as well as (c) the absorption profile for the extended irradiation of a blank, aerated solution of DHA5. An absorption band centered at ca. 408 nm was observed to evolve when DHA5 is photolyzed (λ313 nm) with RDX, which corresponds to the formation of 27. An emission band at approximately 540 nm concomitantly evolved, which can be assigned to emission from 27 based on the emission profile recorded for its N—H analog 26. A ca. 27-fold increase in the emission intensity at 540 nm was generated after 2 minutes of UV irradiation. Similar absorption and emission profiles were obtained for the photoreaction between DHA5 and PETN. Moreover, the presence or absence of oxygen did not noticeably change the observed optical response.

Photolysis of DHA5 under aerobic conditions in the absence of RDX/PETN did not generate a distinct absorbance band at 408 nm. However, electron-rich DHA5 was found to be relatively photostable: 30 minutes of continuous UV irradiation did not result in a noticeable change in the absorption spectrum of DHA5 (FIG. 9C), and its emission peak at 355 nm was found to be bleached by only 10%. Further UV irradiation eventually lead to slight yellowing of DHA5 solutions, and poorly-defined absorbance peaks at 356 nm and ca 440 nm appeared in the absorption spectrum after 2 hours of continuous UV irradiation under air (FIG. 9C). Without wishing to be bound by theory, these new absorption peaks may correspond to the formation of radical cations, N-demethylated species, and/or N-oxide derivatives of DHA5. Notably, a significant portion of this photolyzed DHA5 solution remained unoxidized after 2 hours, and, therefore, the subsequent addition of RDX or PETN nonetheless lead to evolution of a 408 absorbance peak and 540 nm emission peak (5-fold emission turn-on) after a 20 second exposure to 313 nm light.

Figure 10:
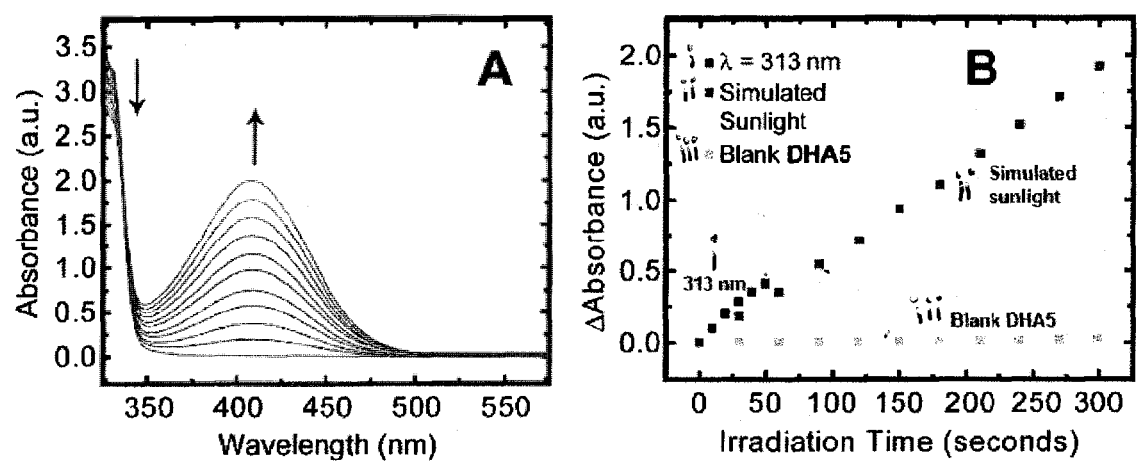
FIG. 10 shows (a) the absorption profile of the photoreaction of DHA5 and RDX in acetonitrile upon exposure to broad-band light from a solar simulator ([DHA5]=$1.3\times10^{-4}$ M. [RDX]=$5.4\times10^{-5}$ M) and (b) a graph showing the rate of formation of the 408 nm absorbance peak in the presence of RDX upon exposure to either simulated sunlight (120 $mW/cm^2$) or monochromatic 313 nm light (10 $mW/cm^2$).

FIG. 10 shows (a) the absorption profile of the photoreaction of DHA5 and RDX in acetonitrile upon exposure to broad-band light from a solar simulator ([DHA5]=$1.3 \times 10^{-4}$ M. [RDX]=$5.4 \times 10^{-5}$ M) and (b) a graph showing the rate of formation of the 408 nm absorbance peak in the presence of RDX upon exposure to either simulated sunlight (120 mW/cm$^2$) or monochromatic 313 nm light (10 mW/cm$^2$). Exposing a mixture of DHA5 and RDX to broad-band light from a solar simulator led to the evolution of the same 408 nm peak observed with irradiation at 313 nm. The rate of formation of the 408 nm peak upon exposure to simulated sunlight also matched that observed upon exposure to monochromatic 313 nm light from a xenon arc lamp. (FIG. 10B). Therefore, simulated sunlight was selected as the light source in subsequent studies to illustrate that the DHAs can function as technology-unintensive, fluorogenic indicators for RDX/PETN under ambient sunlight.

Figure 11:
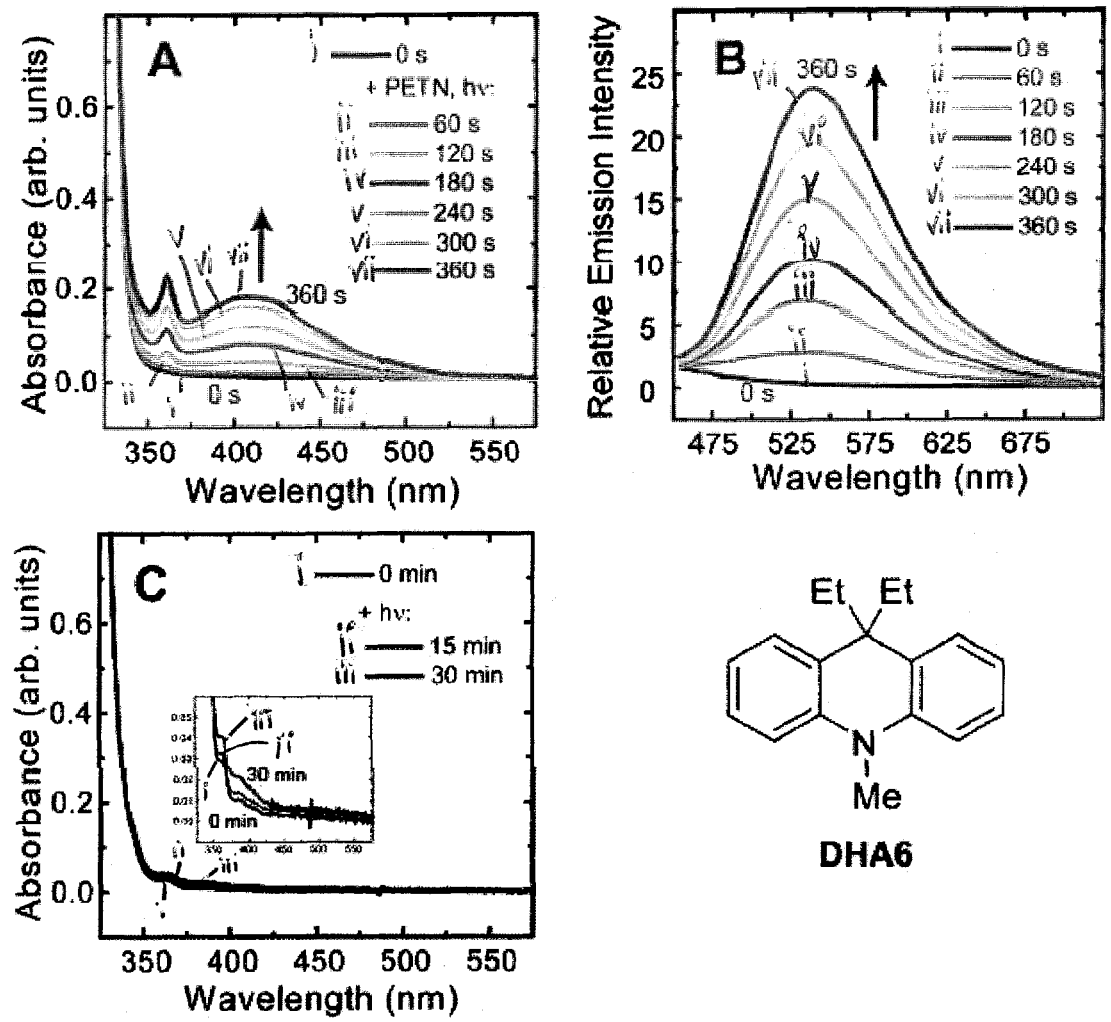
FIG. 11 shows the (a) absorption and (b) emission (B, $\lambda_{ex}$=415 nm) profiles of the photoreaction of DHA6 with PETN in acetonitrile upon exposure to simulated sunlight ([DHA6]=$1.3\times10^{-4}$ M. [PETN]=$5.4\times10^{-5}$ M), as well as (c) the absorption profile for the extended irradiation of a blank, aerated solution of DHA6.

FIG. 11 shows the (a) absorption and (b) emission (B, $\lambda_{ex}$=415 nm) profiles of the photoreaction of DHA6 with PETN in acetonitrile upon exposure to simulated sunlight ([DHA6]=$1.3 \times 10^{-4}$ M. [PETN]=$5.4 \times 10^{-5}$ M), as well as (c) the absorption profile for the extended irradiation of a blank, aerated solution of DHA6. DHA6 behaved similarly to DHA5 in terms of its optical response. Specifically, an absorbance peak at 409 nm evolved in the presence of either RDX or PETN, accompanied with evolution of an emission band at 540 nm. The presence or absence of oxygen did not affect the observed optical response to RDX/PETN. DHA6 was also found to be relatively photostable, with no change in its absorption spectrum and a 5% bleaching of its emission band at 382 nm observed after 30 minutes of continuous exposure to sunlight. The only significant difference between DHA5 and DHA6 was the rate of formation of the 409 nm/540 nm absorption/emission peaks. DHA5 was found to yield a turn-on signal approximately three times faster than DHA6. Without wishing to be bound by theory, this comparatively slow response may be attributed to DHA6 forming a mixture of 32 and 34 upon reacting with RDX/PETN. (FIG. 8).

Figure 12:
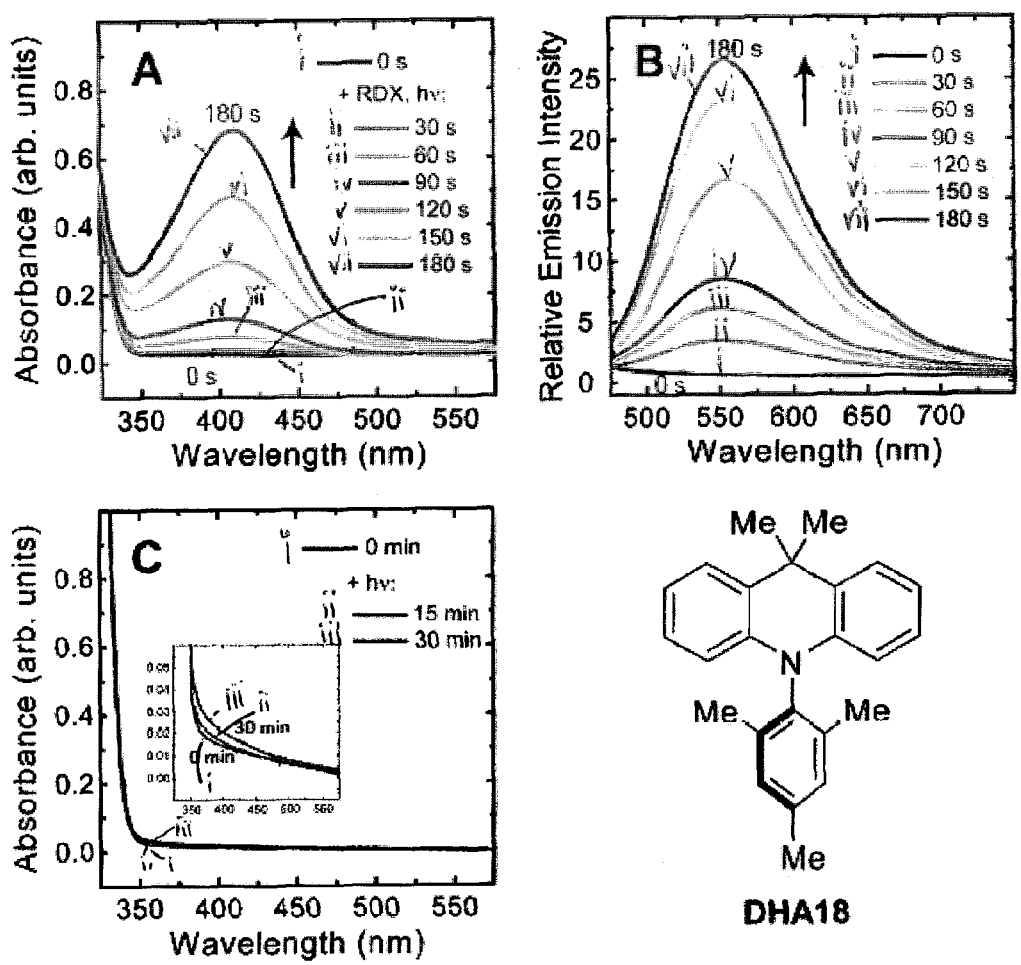
FIG. 12 shows the (a) absorption and (b) emission (B, $\lambda_{ex}$=415 nm) profiles of the photoreaction of DHA18 with RDX in acetonitrile upon exposure to simulated sunlight ([DHA18]=$1.3\times10^{-4}$ M. [RDX]=$5.4\times10^{-5}$ M), as well as (c) the absorption profile for the extended irradiation of a blank, aerated solution of DHA18.

FIG. 12 shows the (a) absorption and (b) emission (B, $\lambda_{ex}$=415 nm) profiles of the photoreaction of DHA18 with RDX in acetonitrile upon exposure to simulated sunlight ([DHA18]=$1.3 \times 10^{-4}$ M. [RDX]=$5.4 \times 10^{-5}$ M), as well as (c) the absorption profile for the extended irradiation of a blank, aerated solution of DHA18. The optical response of DHA18 to either RDX or PETN was also similar to that of DHA5. An absorbance band at 413 nm and an emission peak at 550 nm evolved upon exposure to simulated sunlight in the presence of either RDX or PETN. DHA18 was also relatively photostable, with no change in its absorption spectrum and a 5% bleach of its emission band at 371 nm observed after continuous exposure to simulated sunlight for 30 minutes. The rate of photoreaction of DHA18 with RDX/PETN was slower than that of DHA5 but faster than that of DHA6.

Figure 13:
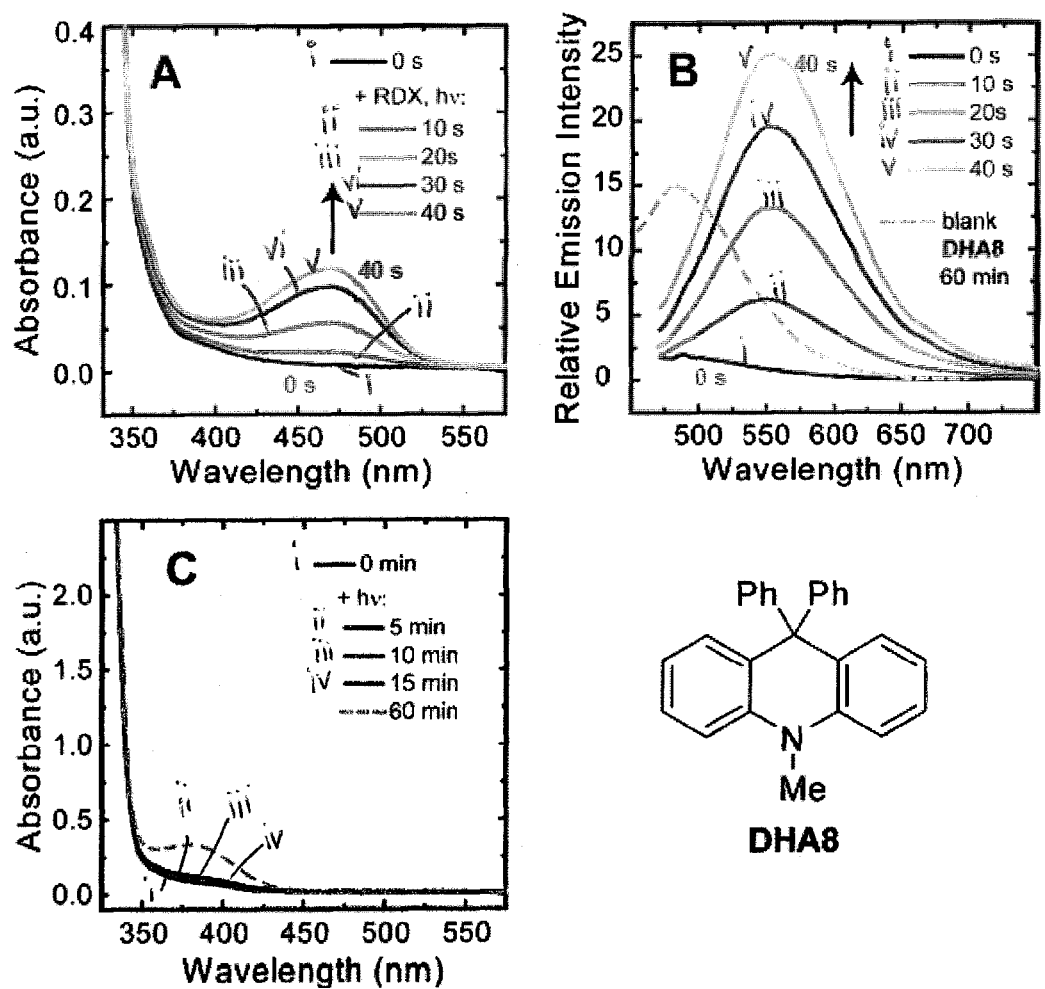
FIG. 13 shows (a) the absorption profile and (b) emission (B, $\lambda_{ex}$=470 nm) profile of the photoreaction of DHA8 with RDX in acetonitrile upon exposure to simulated sunlight ([DHA8]=$1.3\times10^{-4}$ M. [RDX]=$5.4\times10^{-5}$ M), as well as (c) the absorption profile for the irradiation of a blank, aerated solution of DHA8.

FIG. 13 shows (a) the absorption profile and (b) emission (B, $\lambda_{ex}$=470 nm) profile of the photoreaction of DHA8 with RDX in acetonitrile upon exposure to simulated sunlight ([DHA8]=$1.3 \times 10^{-4}$ M. [RDX]=$5.4 \times 10^{-5}$ M). In FIG. 13B, the dashed line depicts the emission spectrum obtained for a blank solution of DHA8 after irradiation under either aerobic or anaerobic conditions for 60 minutes. FIG. 13C shows the absorption profile for the irradiation of a blank, aerated solution of DHA8; the same profile was also obtained for oxygen-free solutions of DHA8. 9,9-Diphenyl-substituted DHA8 differed slightly from the other DHAs explored in this work, as an absorbance band centered at 470 nm, as opposed to ca. 410 nm, evolved during its photoreaction with either RDX or PETN. Based on accompanying GC-MS analyses, this absorbance band was assigned to the formation of 29. An emission band at 550 nm was also observed to evolve concomitantly. An approximately 25-fold increase in the emission intensity at 550 nm was generated in the presence of either RDX or PETN upon exposure to simulated sunlight for 40 seconds. The rates of reaction of DHA5 and DHA8 with RDX/PETN were approximately similar.

Unlike DHA5, DHA6 and DHA18, exposing solutions of DHA8 to sunlight (or monochromatic UV light) in either the presence or absence of oxygen led to the formation of a distinct absorbance band at 380 nm, with an accompanying emission band centered at 478 nm. The same photoreactivity was also observed for other DHAs that contained at least one phenyl substituent in the 9-position (DHA4, DHA11 and DHA13). Since these absorption/emission bands were observed to evolve even in the absence of oxygen, they may not have been generated by simple photooxidation products of DHA8. Moreover, the evolution of the absorbance band at 380 nm is likely not attributed to a photodimerization event, as the product of such a reaction (e.g., D1) has an absorption maximum of 457 nm. (FIG. 7) Without wishing to be bound by theory, the photoproduct responsible for the 380 nm/478 nm absorption/emission peak may be produced by a photocyclization reaction occurs in DHAs with at least one phenyl substituent in the 9-position. Nevertheless, it can be seen in FIG. 13 that the competing photoreaction in blank solutions of DHA8 (dashed green line) is slower than the photonitration of DHA8 in the presence of RDX/PETN and an emission peak at 550 nm is cleanly generated by these explosives in under 10 seconds.

Figure 14:
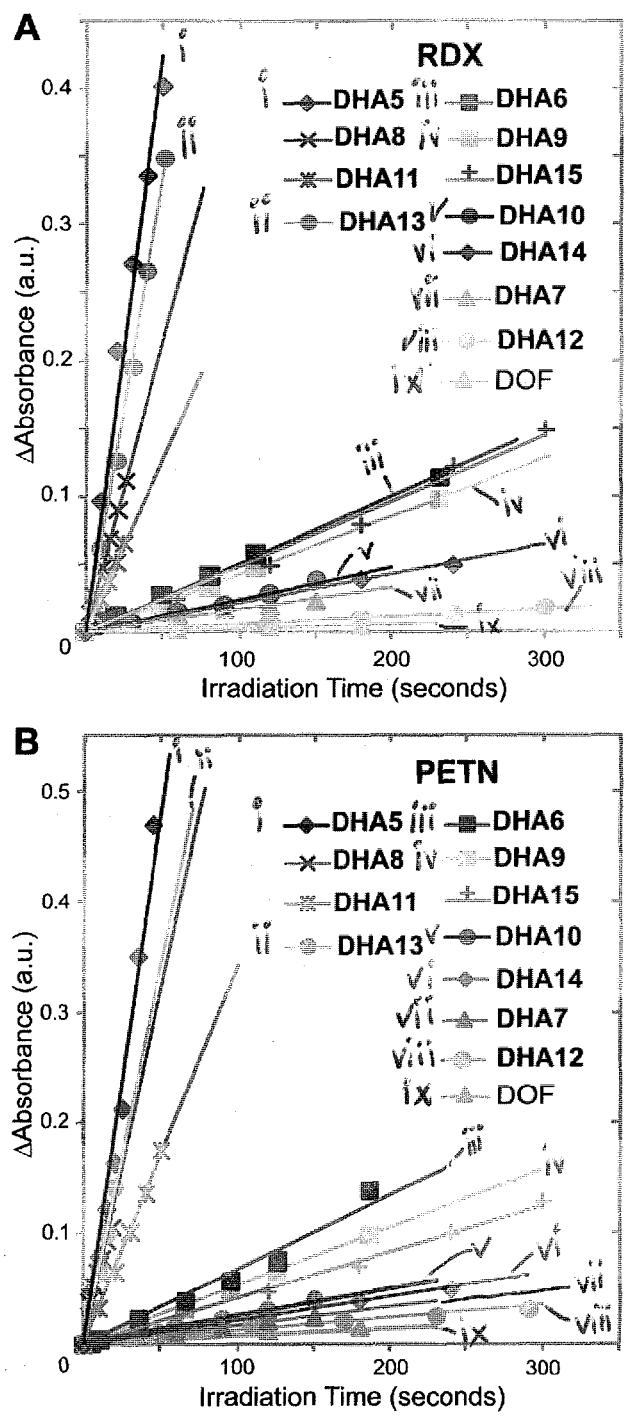
FIG. 14 shows the rates of evolution of the absorbance peak at 410 nm (470 nm for DHA8) for the photoreactions between DHA5-15 and (a) RDX or (b) PETN.

A notable difference between the DHAs in the above Examples involves the rate of formation of the nitrated photoproducts upon reaction with RDX or PETN. By following the evolution of the characteristic low-energy charge transfer band (centered at ca. 400 nm) of the nitrated DHAs with irradiation time, differences in the reactivities of DHA1-18 were identified. (FIGS. 14 and 15) The effect of the substituents at the 9-position of DHAs on their photoreactions with RDX and PETN were studied. FIG. 14 shows the rates of evolution of the absorbance peak at 410 nm (470 nm for DHA8) for the photoreactions between DHA5-15 and (a) RDX or (b) PETN. In FIG. 14, "DOF" refers to 9,9-dioctylfluorene, which was used as a negative control. As can be seen in FIG. 14, the substituents at the 9-position of DHAs significantly affected their reactivities. DHAs with at least one methyl or phenyl substituent at the 9-position were rapidly nitrated in the presence of RDX or PETN. DHAs with alkyl (other than methyl) substituents at the 9-position displayed relatively slower rates of nitration, with isopropyl substituents leading to the slowest reaction rates. Replacing the 9-methyl substituents with trifluoromethyl moieties also retarded the reaction rate. Nominally faster reaction rates were generally observed with PETN over RDX for all DHAs. 9,9-Dioctylfluorene was used as a negative control for these studies and, in all cases, the DHAs reported in this work yielded a significant absorption signal at 400 nm over background.

Figure 15:
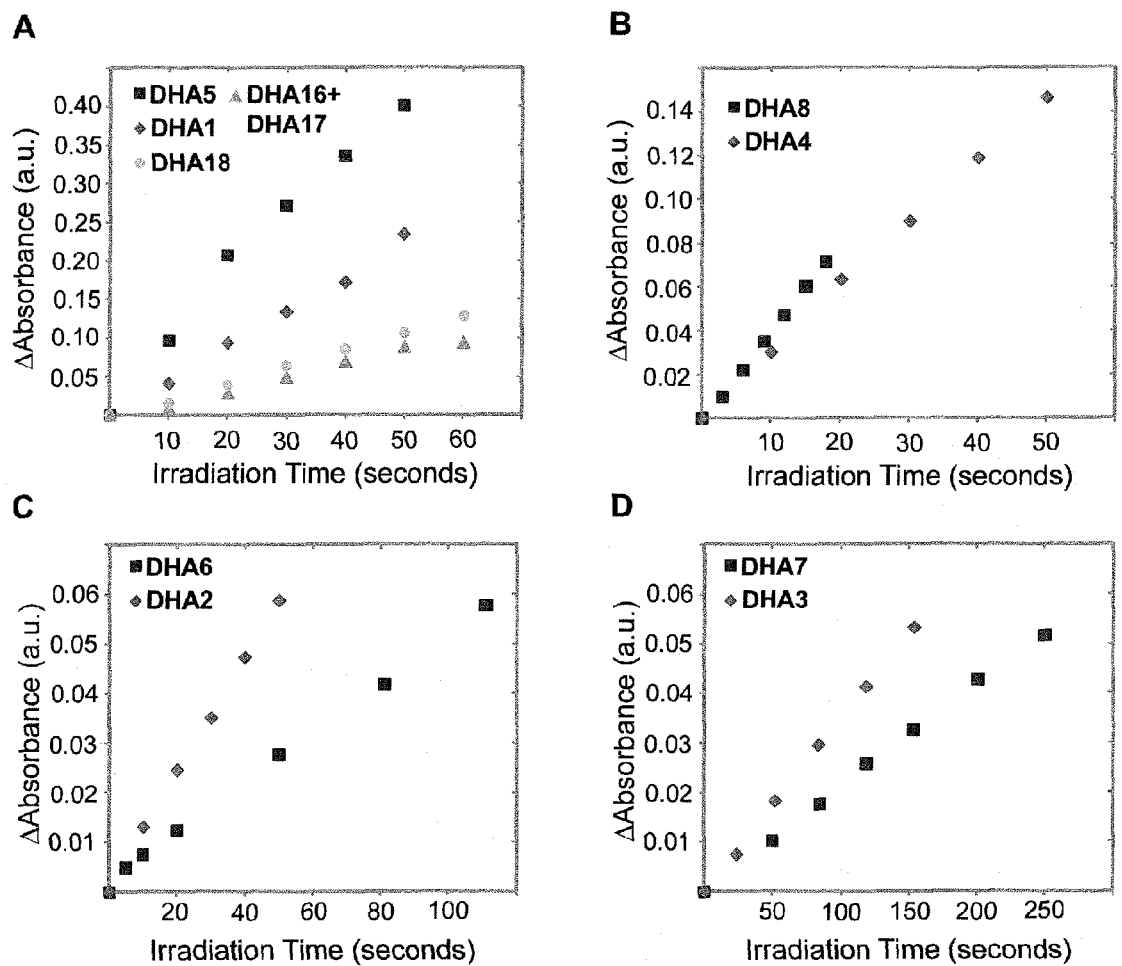
FIG. 15 shows graphs of the rates of evolution of the absorbance peak at 410 nm (470 nm for DHA8) for the photoreactions between various DHAs and RDX, including (a) DHA1, DHA5, DHA16+DHA17, and DHA18; (b) DHA4 and DHA8; (c) DHA2, and DHA6; and (d) DHA3 and DHA7.

The nature of the N-substituent was also found to affect the rate of photonitration in the presence of RDX/PETN. FIG. 15 shows graphs of the rates of evolution of the absorbance peak at 410 nm (470 nm for DHA8) for the photoreactions between various DHAs and RDX. For DHAs with ethyl or isopropyl substituents at the 9-position, the N—H analogues reacted faster the N—Me analogues. For DHAs with phenyl or methyl substituents in the 9-position, this trend was reversed and N—Me analogues displayed the fastest reaction rates. Moreover, N-arylation was found to significantly retard the rate of photonitration.

Lastly, the rate of formation of nitrated DHAs was compared to the formation of

Figure 16:
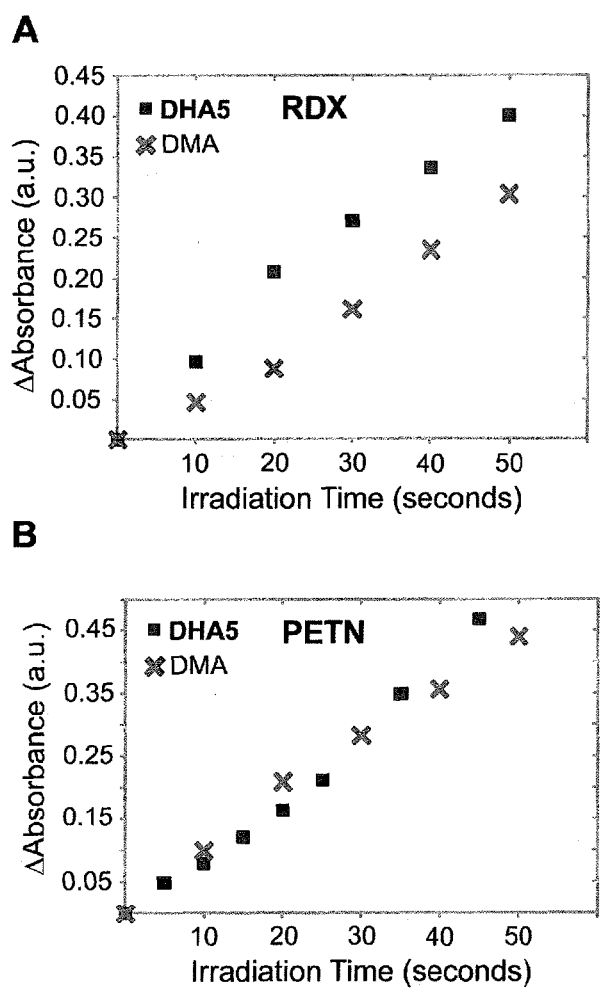
FIG. 16 shows graphs comparing the rates of nitration of DHA5 vs. DMA in the presence of (a) RDX and (b) PETN. The reactivity of DHA5, which displayed the fastest rate of nitration among DHA1-18, was observed to be comparable to that of DMA.

DMNA from DMA. FIG. 16 shows graphs comparing the rates of nitration of DHA5 vs. DMA in the presence of (a) RDX and, (b) PETN. The reactivity of DHA5, which displayed the fastest rate of nitration among DHA1-18, was observed to be comparable to that of DMA.

Example 37

In the following example, RDX/PETN detection in the solid state was investigated. Based on the previously-detailed rates of nitration of DHA1-18 by the photofragmentation products of RDX and PETN, DHA5, DHA8, DHA11 and DHA13 were initially selected as potential indicators for RDX and PETN, as they displayed the fastest rates of reaction. Between these four DHAs, DHA5 and DHA8 were favored because their nitrated products displayed high fluorescence quantum yields. DHA5 was used to demonstrate detection of RDX/PETN in the solid state; however, similar results and detection limits were also obtained with DHA8.

In order to evaluate the utility of DHA5 as a fluorescent indicator for RDX and PETN, the solid-state response of DHA5 to RDX and PETN was investigated. For this study, glass slides coated with DHA5 were prepared by dipcoating into $8 \times 10^{-3}$ M solutions of the indicator in acetonitrile and air drying. RDX and PETN solutions of varying concentration were spotted onto the surface and the slides then irradiated with a solar simulator for no longer than 120 seconds.

Figure 17:
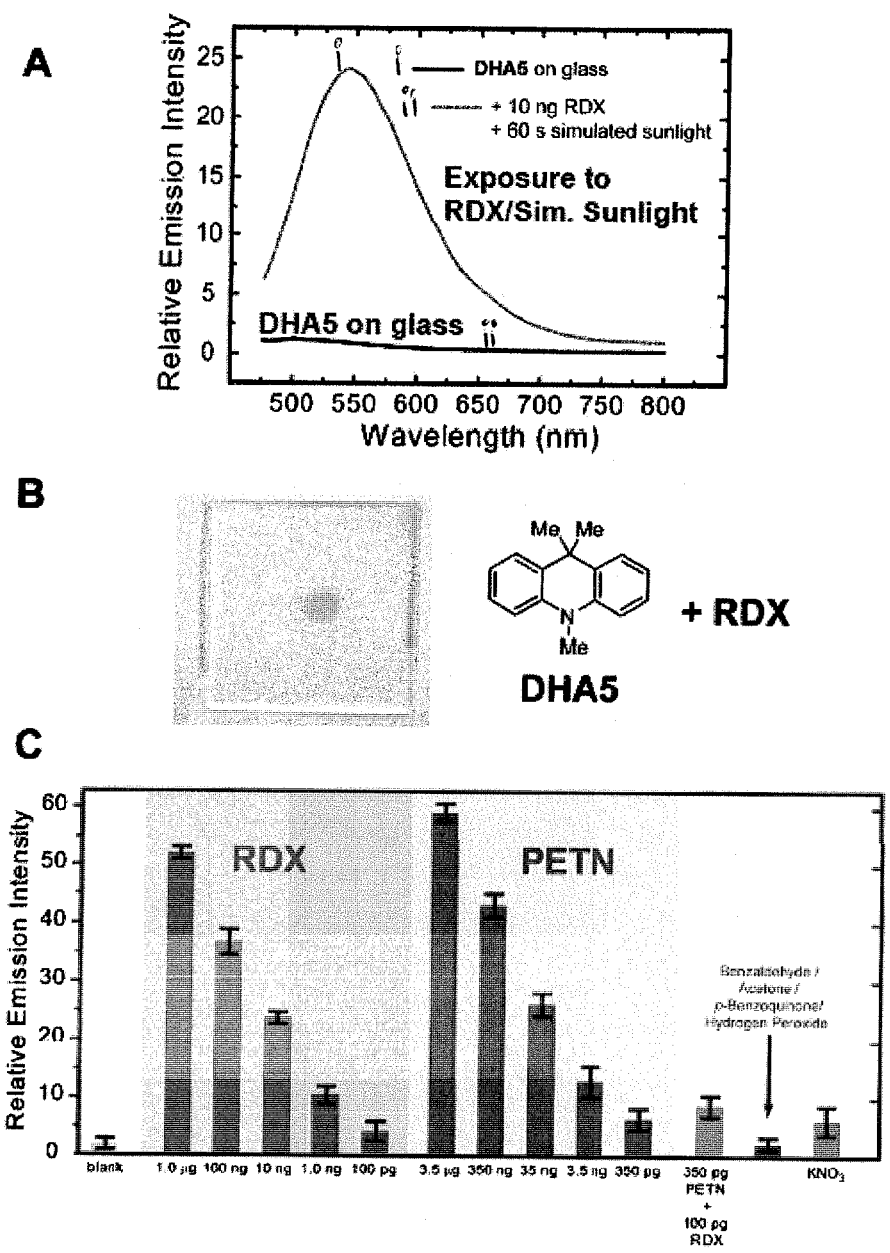
FIG. 17 shows (a) the emission profile ($\lambda_{ex}$ 420 nm) of a glass slide coated with DHA5 and the same slide after spotting with ca. 10 ng of RDX and irradiating with a solar simulator for 60 seconds; (b) a picture of a glass slide coated with DHA5, spotted with ca. 10 ng RDX and exposed to simulated sunlight for 120 s; and (c) a graphs of the relative emission intensity in the solid-state detection of RDX and PETN as measured by monitoring the change in emission intensity at 540 nm upon exposure (60 s) to simulated sunlight.

FIG. 17 shows (a) the emission profile ($\lambda_{ex}$ 420 nm) of a glass slide coated with DHA5 and the same slide after spotting with ca. 10 ng of RDX and irradiating with a solar simulator for 60 seconds; (b) a picture of a glass slide coated with DHA5, spotted with ca. 10 ng RDX and exposed to simulated sunlight for 120 s; and (c) a graphs of the relative emission intensity in the solid-state detection of RDX and PETN as measured by monitoring the change in emission intensity at 540 nm upon exposure (60 s) to simulated sunlight. In the case of potassium nitrate, a concentrated solution (30 mM) in acetonitrile and long exposure times (600 s) were necessary to obtain the 8-fold increase shown.

As shown in FIG. 17A, a turn-on emission signal (e.g., an increase in signal relative to the DHA5-coated glass slide prior to exposure to analyte) at 540 nm was generated by 10 ng of RDX after 60 seconds of irradiation with a solar simulator. In addition to a fluorescence signal, the distinct yellow color of 27 could also be observed by eye, as shown in FIG. 17B. The limits of detection of the DHA5 chemosensor were estimated by spotting RDX or PETN solutions of varying concentrations onto the DHA5-coated slides and are shown in FIG. 17C. In general, a greater emission signal at 540 nm was generated by PETN over RDX, possibly because PETN is more susceptible to photodegradation than RDX.

Select interferents, such as ketones and aldehydes, did not produce a significant emission signal at 540 nm. Moreover, consistent with observations made during the synthesis of D1, hydrogen peroxide did not react readily with DHA5 and most likely only formed a small quantity of the radical cation of DHA5, which is non-emissive and therefore did not produce any emission at 540 nm.

Aqueous potassium nitrate solutions of varying concentrations were also spotted onto the DHA5-coated glass slides in order to gauge the response of the DHA5 indicator to nitrate contaminants. Consistent with previous observations, sub-micromolar solutions of potassium nitrate did not generate a significant emission signal at 540 nm after one hour in either the absence of presence of simulated solar irradiation. Using a 30 mM solution of potassium nitrate, an approximately 8-fold increase in the emission intensity at 540 nm was observed after a 10 minute exposure to simulated sunlight. However, given the high nitrate concentration and relatively long irradiation time necessary to effect this emission signal, interference from nitrates during RDX/PETN detection can likely be surmounted.

Within experimental error, approximately 100 pg of RDX and PETN can be detected by the DHA5 indicator under aerobic conditions by monitoring the emission intensity at 540 nm. In the presence of nitrate interferents, this detection limit is conservatively estimated as ca. 1 ng. These detection limits are competitive with present transportation security systems that make use of swipes to collect particles.

What is claimed is:

1. A sensor, comprising:
   a compound comprising the structure,

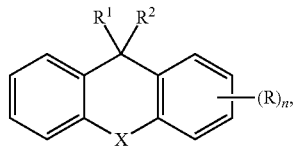

wherein X is a heteroatom optionally substituted with hydrogen, alkyl, heteroalkyl, alkenyl, heteroalkenyl, alkynyl, heteroalkynyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, or heteroaryl, any of which is optionally substituted; and n is 0-8;

a source of energy applicable to the compound to cause an emission of radiation; and an emission detector positioned to detect the emission.

2. A sensor as in claim 1, wherein $R^1$ and $R^2$ are can be the same or different and are alkyl or aryl, any of which is optionally substituted.

3. A sensor as in claim 1, wherein $R^1$ and $R^2$ are alkyl.

4. A sensor as in claim 1, wherein $R^1$ and $R^2$ are aryl.

5. A sensor as in claim 1, wherein $R^1$ and $R^2$ are phenyl.

6. A sensor as in claim 1, wherein at least two R groups are joined together to form a cycloalkyl, heterocycloalkyl, aryl, or heteroaryl ring, any of which is optionally substituted.

7. A sensor as in claim 1, wherein X is nitrogen, oxygen, sulfur, or phosphorus, any of which is optionally substituted.

8. A sensor as in claim 1, wherein X is an optionally substituted nitrogen.

9. A sensor as in claim 1, wherein the compound has the structure,

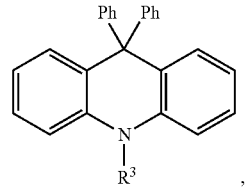

wherein $R^3$ is hydrogen or alkyl.

10. A sensor as in claim 1, wherein the compound has the structure,

[structure: 9,9-diphenyl-9,10-dihydroacridine with N-H]

11. A sensor as in claim 1, wherein the compound has the structure,

[structure: 9,9-diphenyl-10-methyl-9,10-dihydroacridine with N-CH₃]

12. A sensor as in claim 1, wherein the compound is in solution.

13. A sensor as in claim 1, further comprising a support material, wherein the compound is dispersed within the support material.

14. A sensor as in claim 1, wherein the support material is a polymer.

15. A sensor as in claim 14, wherein the polymer is poly (methyl methacrylate), polyethylene, polypropylene, poly (vinyl chloride), poly(vinyl benzoate), poly(vinyl acetate), cellulose, corn starch, poly(vinyl pyrrolidinone), polyacrylamide, epoxy, silicone, poly(vinyl butyral), polyurethane, nylon, polyacetal, polycarbonate, polyester, polyether, polybutadiene, or combinations thereof.

16. A sensor as in claim 14, wherein the polymer is poly (methylmethacrylate), poly(vinylpyrrolidinone), or poly(4-vinylpyridine).

17. A sensor as in claim 14, wherein the polymer is poly (methylmethacrylate).

18. A sensor as in claim 14, wherein the polymer is poly (vinylpyrrolidinone).

19. A sensor as in claim 1, wherein the source of energy, when applied to the compound, causes the analyte to generate a species capable of interacting with the compound via a nitration reaction.

20. A sensor as in claim 1, wherein the source of energy is an electric, magnetic, optical, acoustic, electromagnetic, or mechanical field.

21. A sensor as in claim 1, wherein the source of energy is electromagnetic radiation.

22. A sensor, comprising:
a material comprising a compound capable of accepting a nitro equivalent upon exposure to a nitro-containing analyte;
a source of energy applicable to the material to cause an emission of radiation; and
an emission detector positioned to detect the emission.

23. A sensor as in claim 22, wherein the nitro-containing analyte is 2,4,6-hexahydro-1,3,5-triazinane (RDX),2,3-dimethyl-2,3-dinitrobutane (DMNB), 2,2-bis[(nitrooxy)-methyl]-1,3-propanediol dinitrate ester (PETN), or 1,3,5,7-tetranitroperhydro-1,3,5,7-tetrazocine (HMX).

24. A sensor as in claim 22, wherein the nitro-containing analyte is 2,4,6-hexahydro-1,3,5-triazinane (RDX).

25. A sensor as in claim 22, wherein the nitro-containing analyte is 22,2-bis[(nitrooxy)-methyl]-1,3-propanediol dinitrate ester (PETN).

26. A sensor as in claim 22, wherein the compound comprises the structure,

[structure with R¹, R², X, (R)ₙ substituents on dihydroacridine-like core]

wherein X is a heteroatom optionally substituted with hydrogen, alkyl, heteroalkyl, alkenyl, heteroalkenyl, alkynyl, heteroalkynyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, or heteroaryl, any of which is optionally substituted; and n is 0-8.

27. A sensor as in claim 26, wherein $R^1$ and $R^2$ are can be the same or different and are alkyl or aryl, any of which is optionally substituted.

28. A sensor as in claim 26, wherein $R^1$ and $R^2$ are alkyl.

29. A sensor as in claim 26, wherein $R^1$ and $R^2$ are aryl.

30. A sensor as in claim 26, wherein $R^1$ and $R^2$ are phenyl.

31. A sensor as in claim 26, wherein at least two R groups are joined together to form a cycloalkyl, heterocycloalkyl, aryl, or heteroaryl ring, any of which is optionally substituted.

32. A sensor as in claim 26, wherein X is nitrogen, oxygen, sulfur, or phosphorus, any of which is optionally substituted.

33. A sensor as in claim 26, wherein X is an optionally substituted nitrogen.

34. A sensor as in claim 22, wherein the compound has the structure,

[structure: 9,9-diphenyl-9,10-dihydroacridine with N-R³]

wherein $R^3$ is hydrogen or alkyl.

35. A sensor as in claim 22, wherein the compound has the structure,

[structure: 9,9-diphenyl-9,10-dihydroacridine with N-H]

36. A sensor as in claim 22, wherein the compound has the structure,

[structure: 9,9-diphenyl-10-methylacridine]

37. A sensor as in claim 22, wherein the compound is in solution.
38. A sensor as in claim 22, further comprising a support material, wherein the compound is dispersed within the support material.
39. A sensor as in claim 22, wherein the support material is a polymer.
40. A sensor as in claim 39, wherein the polymer is poly (methyl methacrylate), polyethylene, polypropylene, poly (vinyl chloride), poly(vinyl benzoate), poly(vinyl acetate), cellulose, corn starch, poly(vinyl pyrrolidinone), polyacrylamide, epoxy, silicone, poly(vinyl butyral), polyurethane, nylon, polyacetal, polycarbonate, polyester, polyether, polybutadiene, or combinations thereof.
41. A sensor as in claim 39, wherein the polymer is poly (methylmethacrylate), poly(vinylpyrrolidinone), or poly(4-vinylpyridine).
42. A sensor as in claim 39, wherein the polymer is poly (methylmethacrylate).
43. A sensor as in claim 39, wherein the polymer is poly (vinylpyrrolidinone).
44. A sensor as in claim 22, wherein the source of energy, when applied to the compound, causes the analyte to generate a species capable of interacting with the compound via a nitration reaction.
45. A sensor as in claim 22, wherein the source of energy is an electric, magnetic, optical, acoustic, electromagnetic, or mechanical field.
46. A sensor as in claim 22, wherein the source of energy is electromagnetic radiation.
47. A method for determining an analyte, comprising:
exposing a material to a sample suspected of containing an analyte, wherein the analyte, if present, interacts with the material via a nitration reaction to produce a nitro-containing compound having a luminescence emission; and
determining the luminescence emission of the compound, thereby determining the analyte.
48. A method as in claim 47, further comprising:
exposing the analyte to a source of energy such that the analyte produces a species capable of interacting with the compound via a nitration reaction.
49. A method as in claim 48, wherein the species is a $NO_x$ species, where x is at least 1.
50. A method as in claim 48, wherein the source of energy is an electric, magnetic, optical, acoustic, electromagnetic, or mechanical field.
51. A method as in claim 48, wherein the source of energy is electromagnetic radiation.
52. A method as in claim 47, wherein the analyte is 2,4,6-hexahydro-1,3,5-triazinane (RDX), 2,3-dimethyl-2,3-dinitrobutane (DMNC), 2,2-bis[(nitrooxy)-methyl]-1,3-propanediol dinitrate ester (PETN), or 1,3,5,7-tetranitroperhydro-1,3,5,7-tetrazocine (HMX).
53. A method as in claim 47, wherein the analyte is 2,4,6-hexahydro-1,3,5-triazinane (RDX).

54. A method as in claim 47, wherein the analyte is 22,2-bis[(nitrooxy)-methyl]-1,3-propanediol dinitrate ester (PETN).
55. A method as in claim 47, wherein the compound comprises the structure,

[structure with $R^1$, $R^2$, X, $(R)_n$]

wherein X is a heteroatom optionally substituted with hydrogen, alkyl, heteroalkyl, alkenyl, heteroalkenyl, alkynyl, heteroalkynyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, or heteroaryl, any of which is optionally substituted; and n is 0-8.

56. A method as in claim 55, wherein $R^1$ and $R^2$ are can be the same or different and are alkyl or aryl, any of which is optionally substituted.
57. A method as in claim 55, wherein $R^1$ and $R^2$ are alkyl.
58. A method as in claim 55, wherein $R^1$ and $R^2$ are aryl.
59. A method as in claim 55, wherein $R^1$ and $R^2$ are phenyl.
60. A method as in claim 55, wherein at least two R groups are joined together to form a cycloalkyl, heterocycloalkyl, aryl, or heteroaryl ring, any of which is optionally substituted.
61. A method as in claim 55, wherein X is nitrogen, oxygen, sulfur, or phosphorus, any of which is optionally substituted.
62. A method as in claim 55, wherein X is an optionally substituted nitrogen.
63. A method as in claim 47, wherein the compound has the structure,

[structure: 9,9-diphenyl-10-$R^3$-acridine]

wherein $R^3$ is hydrogen or alkyl.
64. A method as in claim 47, wherein the compound has the structure,

[structure: 9,9-diphenylacridine with NH]

65. A method as in claim 47, wherein the compound has the structure,

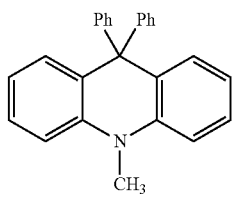

66. A method as in claim 47, wherein the compound is in solution.

67. A method as in claim 47, further comprising a support material, wherein the compound is dispersed within the support material.

68. A method for determination of an analyte, comprising:
exposing a material to a sample suspected of containing an analyte, wherein the analyte, if present, interacts with the material to produce a change in a determinable signal of the material,
wherein the material comprises a compound having the structure,

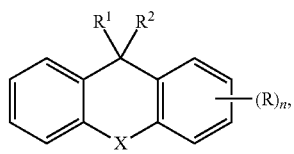

wherein X is a heteroatom optionally substituted with alkyl, heteroalkyl, aryl, or heteroaryl, any of which is optionally substituted; each R can be the same or different and can be alkyl, heteroalkyl, alkenyl, heteroalkenyl, alkynyl, heteroalkynyl, aryl, or heteroaryl, any of which is optionally substituted, or, at least two R groups are joined together to form a ring, optionally substituted; $R_1$ and $R_2$ can be the same or different and are alkyl, heteroalkyl, aryl, or heteroaryl, any of which is optionally substituted; and n is 0-8; and
determining the change in the determinable signal of the material, thereby determining the analyte.

69. A method as in claim 68, wherein the determinable signal is a luminescence emission.

70. A method as in claim 69, wherein the change comprises a change in the wavelength of the luminescence emission.

71. A method as in claim 69, wherein the change comprises a decrease in luminescence intensity.

72. A method as in claim 69, wherein the change comprises an increase in luminescence intensity.

73. A method as in claim 68, further comprising:
exposing the analyte to a source of energy such that the analyte produces a species capable of interacting with the compound via a nitration reaction.

74. A method as in claim 73, wherein the species is a $NO_x$ species, where x is at least 1.

75. A method as in claim 73, wherein the source of energy is an electric, magnetic, optical, acoustic, electromagnetic, or mechanical field.

76. A method as in claim 73, wherein the source of energy is electromagnetic radiation.

77. A method as in claim 68, wherein the analyte is 2,4,6-hexahydro-1,3,5-triazinane (RDX), 2,3-dimethyl-2,3-dinitrobutane (DMND), 2,2-bis[(nitrooxy)-methyl]-1,3-propanediol dinitrate ester (PETN), or 1,3,5,7-tetranitroperhydro-1,3,5,7-tetrazocine (HMX).

78. A method as in claim 68, wherein the analyte is 2,4,6-hexahydro-1,3,5-triazinane (RDX).

79. A method as in claim 68, wherein the analyte is 22,2-bis[(nitrooxy)-methyl]-1,3-propanediol dinitrate ester (PETN).

80. A method as in claim 68, wherein the compound is in solution.

81. A method as in claim 68, further comprising a support material, wherein the compound is dispersed within the support material.

* * * * *